US012747244B2

(12) United States Patent
Chen et al.

(10) Patent No.: US 12,747,244 B2
(45) Date of Patent: Sep. 29, 2026

(54) SYNTHESIS OF BTK INHIBITOR AND INTERMEDIATES THEREOF

(71) Applicant: Merck Sharp & Dohme LLC, Rahway, NJ (US)

(72) Inventors: Yonggang Chen, Westfield, NJ (US); James Corry, South Plainfield, NJ (US); Richard Desmond, Lebanon, NJ (US); Michael J. Di Maso, East Brunswick, NJ (US); Jacob H. Forstater, South Orange, NJ (US); Jeffrey T. Kuethe, Somerset, NJ (US); Nadine Kuhl, Garwood, NJ (US); Reed Larson, Jersey City, NJ (US); Francois Levesque, Morris Plains, NJ (US); Karthik Narsimhan, Waltham, MA (US); Douglas Otte, Chatham, NJ (US); Christopher K. Prier, Newark, NJ (US); Michael Shevlin, Middlesex, NJ (US); Eric Sirota, Hoboken, NJ (US); Lushi Tan, Edison, NJ (US); David A. Thaisrivongs, Westfield, NJ (US); Ben W. H. Turnbull, Jersey City, NJ (US); Zhixun Wang, Springfield, NJ (US); Kaijiong Xiao, Clark, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 287 days.

(21) Appl. No.: 18/563,082

(22) PCT Filed: May 26, 2022

(86) PCT No.: PCT/US2022/030997
§ 371 (c)(1),
(2) Date: Nov. 21, 2023

(87) PCT Pub. No.: WO2022/251404
PCT Pub. Date: Dec. 1, 2022

(65) Prior Publication Data

US 2024/0262834 A1 Aug. 8, 2024

Related U.S. Application Data

(60) Provisional application No. 63/336,367, filed on Apr. 29, 2022, provisional application No. 63/223,693, filed on Jul. 20, 2021, provisional application No. 63/194,307, filed on May 28, 2021.

(51) Int. Cl.
*C07D 487/04* (2006.01)

(52) U.S. Cl.
CPC .................................. *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 8,629,133 | B2 | 1/2014 | Sugimoto et al. |
| 9,109,209 | B2 | 8/2015 | Cabirol |
| 2005/0182055 | A1 | 8/2005 | Berwe et al. |
| 2018/0055846 | A1 | 3/2018 | Bates et al. |
| 2018/0230155 | A1 | 8/2018 | Beaudry et al. |

FOREIGN PATENT DOCUMENTS

| | | | |
|---|---|---|---|
| CN | 112608318 | A | 4/2021 |
| RU | 2715421 | C2 | 2/2020 |
| WO | 2007023381 | A1 | 3/2007 |
| WO | 2007105154 | A2 | 9/2007 |
| WO | 2010099501 | A2 | 9/2010 |
| WO | 2012024104 | A2 | 2/2012 |
| WO | 2013036861 | A1 | 3/2013 |
| WO | 2017103851 | A1 | 6/2017 |
| WO | 2017111787 | A1 | 6/2017 |
| WO | WO2022012510 | A1 * | 1/2022 |
| WO | 2022251402 | A1 | 12/2022 |

OTHER PUBLICATIONS

Valeev et al. (Chemistry of Natural Compounds 2004; 40(6): 521-525) (Year: 2004).*

Di Maso Mike et al: "From Wood Pulp to a Candidate Medicine", ACS Webinars, Sep. 8, 2022 (Sep. 8, 2022), XP093334541,Retrieved from the Internet: URL:https://www.acs.org/content/dam/acsorg/acs-webinars/2022/slides/2022-09-08-nemtabrutinib-gci2.pdf * Slides 15-33 *.

(Continued)

*Primary Examiner* — Brandon J Fetterolf

(74) *Attorney, Agent, or Firm* — Daniel Woods; John C. Todaro

(57) ABSTRACT

The present invention relates to efficient synthetic processes useful in the preparation of Compound A, a BTK inhibitor of Formula (I): or a pharmaceutically acceptable salt thereof, including the preparation of intermediates used to make Compound A or a pharmaceutically acceptable salt thereof.

Formula (I)

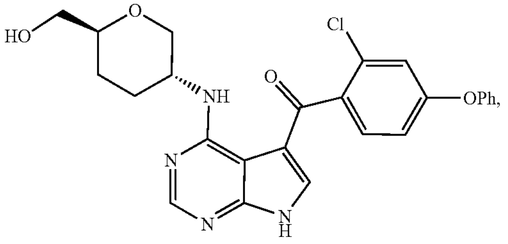

17 Claims, No Drawings

Specification includes a Sequence Listing.

(56) References Cited

OTHER PUBLICATIONS

Gomm, Andrew et al., Transaminases for chiral amine synthesis, Current Opinion in Chemical Biology, 43, 106-112, 2018.
Kelly, Stephen A. et al., Application of ω-Transaminases in the Pharmaceutical Industry, Chem. Rev., 118, 349-367, 2018.
Kuhl, Nadine et al., Utilizing Biocatalysis and an Unprecedented Sulfolane-mediated Reductive Acetal Opening to Access Nemtabrutinib from Cyrene, chemrxiv.org, N/A, 1-7, 2022
Prier, Christopher K. et al., Amination of a Green Solvent via Immobilized Biocatalysis for the Synthesis of Nemtabrutinib, ACS Catal., 13, 7707-7714, 2023.
Amann, Franz et al., Thermal Overman Rearrangement of a Glucal Derivative in a Tube Reactor on Pilot Plant Scale, Org. Process Res. Dev., 20(2), 446-451, 2016.
Dunn, et al. Michael J., Synthesis of Enantiomerically Pure Unsaturated-Amino Acids Using Serine-Derived Zinc/Copper Reagents, J. Org. Chem., 60(7), 2210-2215, 1995.
Kriek, Nicole M. A. J. et al., Synthesis of Novel Tetrahydropyran-Based Dipeptide Isosters by Overman Rearrangement of 2,3-Didehydroglycosides, Eur. J. Org. Chem, 2003(13), 2418-2427, 2003.
Lunse, Christina E. et al., Carba-sugars Activate the glmS-Riboswitch of *Staphylococcus aureus*, ACS Chem. Biol., 6(7), 675-678, 2011.
Valeev, F. A. et al., Synthesis of 2-amino Derivatives of Levoglucosenone, Chemistry of Natural Compounds, 40(6), 521-525, 2004.
Yasuda, Nobuyoshi et al., Practical Asymmetric Synthesis of a Calcitonin Gene-Related Peptide (CGRP) Receptor Antagonist Ubrogepant, Org. Process Res. Dev., 21, 1851-1858, 2017.
Bezsudnova, E. Yu. et al., Properties of Bacterial and Archaean Transaminases of Branched Amino Acids, Biochemistry (Mosc)., 82(13), 1572-1591 Abstract Only, 2017.

* cited by examiner

SEQUENCE LISTING

```
<160> NUMBER OF SEQ ID NOS: 8

<210> SEQ ID NO 1
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Trp Val Ala Ile Thr
        115                 120                 125

Arg Gly Tyr Ser Ser Thr Pro Leu Glu Arg Asp Val Thr Lys His Arg
    130                 135                 140

Pro Gln Val Tyr Met Tyr Ala Val Pro Tyr Gln Trp Ile Val Pro Phe
145                 150                 155                 160
```

-continued

```
Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Ala Ala
            180                 185                 190

Gly Asp Leu Ile Arg Ala Ile Gln Glu Thr His Asp Arg Gly Phe Glu
        195                 200                 205

Leu Pro Leu Leu Leu Asp Phe Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Arg Asp Ala Asp Glu Val Leu Gly Cys Ser Thr Ala Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Cys Leu Leu Thr Pro Val Gln Tyr
                325                 330


<210> SEQ ID NO 2
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Phe Ser Leu Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Ile Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Ile Val Trp Val Ala Ile Thr
        115                 120                 125

Arg Gly Tyr Ser Ser Thr Pro Leu Glu Arg Asp Val Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Ala Ala
            180                 185                 190
```

```
Gly Asp Leu Ile Arg Ala Ile Gln Glu Thr His Asp Arg Gly Phe Glu
        195                 200                 205

Leu Pro Leu Leu Leu Asp Phe Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Arg Asp Ala Asp Glu Val Leu Gly Cys Ser Thr Ala Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Cys Leu Leu Thr Pro Val Gln Tyr
                325                 330


<210> SEQ ID NO 3
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Phe Ser Leu Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Val Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Trp Val Ala Ile Thr
        115                 120                 125

Arg Gly Tyr Ser Ser Thr Pro Leu Glu Arg Asp Val Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Ala Ala
            180                 185                 190

Gly Asp Leu Ile Arg Ala Ile Gln Glu Thr His Asp Arg Gly Phe Glu
        195                 200                 205

Leu Pro Leu Leu Leu Asp His Asp Asn Leu Leu Ala Glu Gly Pro Gly
```

```
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Arg
                245                 250                 255

Ser Leu Gly His Glu Ala Ile Leu Ala Asp Ile Thr Pro Ala Glu Leu
            260                 265                 270

Arg Asp Ala Asp Glu Val Leu Gly Cys Ser Thr Ala Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Cys Leu Leu Thr Pro Val Gln Tyr
                325                 330


<210> SEQ ID NO 4
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Phe Ser Leu Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Val Phe Asp Gln Gly Phe Tyr Thr Ser Asp
    50                  55                  60

Ala Thr Tyr Thr Val Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Trp Val Ala Ile Thr
        115                 120                 125

Arg Gly Tyr Ser Ser Thr Pro Leu Glu Arg Asp Val Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Ala Ser
            180                 185                 190

Ile Asp Leu Ile Arg Ala Ile Gln Glu Thr His Asp Arg Gly Phe Glu
        195                 200                 205

Leu Pro Leu Leu Leu Asp His Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240
```

```
Ala Ala Leu Pro Gly Ile Thr Arg Lys Thr Val Leu Glu Ile Ala Glu
                245                 250                 255

Ser Leu Gly His Glu Ala Met Leu Ala Asp Ile Thr Pro Ala Glu Leu
            260                 265                 270

Arg Asp Ala Asp Glu Val Leu Gly Cys Ser Thr Ala Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Cys Leu Leu Thr Pro Val Gln Tyr
                325                 330


<210> SEQ ID NO 5
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Phe Ser Leu Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
        35                  40                  45

Ser Glu Ala Arg Ile Ser Val Phe Asp Gln Gly Phe Tyr Thr Ser Asp
    50                  55                  60

Ala Thr Tyr Thr Ala Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Trp Val Ala Ile Thr
        115                 120                 125

Arg Gly Tyr Ser Ser Thr Pro Leu Glu Arg Asp Val Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Ala Ser
            180                 185                 190

Ile Asp Leu Ile Arg Ala Ile Gln Glu Thr His Asp Arg Gly Phe Glu
        195                 200                 205

Leu Pro Leu Leu Leu Asp His Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Met Leu Ala Asp Ile Thr Pro Ala Glu Leu
            260                 265                 270
```

```
Arg Asp Ala Asp Glu Val Leu Gly Cys Ser Thr Ala Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320

Pro Ser Cys Leu Leu Thr Pro Val Gln Tyr
                325                 330


<210> SEQ ID NO 6
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Phe Ser Leu Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Val
        35                  40                  45

Ser Glu Ala Arg Ile Ser Val Phe Asp Gln Gly Phe Tyr Ala Ser Asp
    50                  55                  60

Ala Thr Tyr Thr Ala Phe His Val Trp Asn Gly Asn Ala Phe Arg Leu
65                  70                  75                  80

Gly Asp His Ile Glu Arg Leu Trp Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Gly Val Ala Ile Thr
        115                 120                 125

Arg Gly Tyr Ser Ser Thr Pro Leu Glu Arg Asp Val Thr Lys His Arg
    130                 135                 140

Pro Gln Val Tyr Met Tyr Ala Val Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Ala Ser
            180                 185                 190

Ile Asp Leu Ile Arg Ala Ile Gln Glu Thr His Asp Arg Gly Phe Glu
        195                 200                 205

Leu Pro Leu Leu Leu Asp His Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Arg
                245                 250                 255

Ser Leu Gly His Glu Ala Met Leu Ala Asp Ile Thr Pro Ala Glu Leu
            260                 265                 270

Arg Asp Ala Asp Glu Val Leu Gly Cys Ser Thr Ala Gly Gly Val Trp
        275                 280                 285

Pro Phe Val Ser Val Asp Gly Asn Ser Ile Ser Asp Gly Val Pro Gly
```

```
    290                 295                 300

Pro Val Thr Gln Ser Ile Ile Arg Arg Tyr Trp Glu Leu Asn Val Glu
305                 310                 315                 320

Pro Ser Cys Leu Leu Thr Pro Val Gln Tyr
                325                 330


<210> SEQ ID NO 7
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Phe Ser Leu Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Val
        35                  40                  45

Ser Glu Ala Arg Ile Ser Val Phe Asp Gln Gly Phe Tyr Ala Ser Asp
    50                  55                  60

Ala Thr Tyr Thr Ala Phe His Val Trp Asn Gly Asn Ala Phe Arg Leu
65                  70                  75                  80

Gly Asp His Ile Glu Arg Leu Trp Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Gly Val Val Ile Thr
        115                 120                 125

Arg Gly Tyr Ser Ser Thr Pro Leu Glu Arg Asp Val Thr Lys His Arg
    130                 135                 140

Pro Gln Val Tyr Met Tyr Ala Ile Pro Tyr Gln Trp Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Ala Ser
            180                 185                 190

Ile Asp Leu Ile Arg Ala Ile Gln Glu Thr His Asp Arg Gly Phe Glu
        195                 200                 205

Leu Pro Leu Leu Leu Asp His Asp Asn Leu Leu Ala Glu Gly Pro Gly
    210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Arg
                245                 250                 255

Ser Leu Gly His Glu Ala Met Leu Ala Asp Ile Thr Pro Ala Glu Leu
            260                 265                 270

Arg Asp Ala Asp Glu Val Leu Gly Cys Ser Thr Ala Gly Gly Val Trp
        275                 280                 285

Pro Phe Val Ser Val Asp Gly Asn Ser Ile Ser Asp Gly Val Pro Gly
    290                 295                 300

Pro Val Thr Gln Ser Ile Ile Arg Arg Tyr Trp Glu Leu Asn Val Glu
305                 310                 315                 320
```

Pro Ser Cys Leu Leu Thr Pro Val Gln Tyr
325 330

<210> SEQ ID NO 8
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Met Ala Phe Ser Leu Asp Thr Pro Glu Ile Val Tyr Thr His Asp Thr
1 5 10 15

Gly Leu Asp Tyr Ile Thr Tyr Ser Asp Tyr Glu Leu Asp Pro Ala Asn
20 25 30

Pro Leu Ala Gly Gly Ala Ala Trp Ile Glu Gly Ala Phe Val Pro Pro
35 40 45

Ser Glu Ala Arg Ile Ser Val Phe Asp Gln Gly Phe Tyr Thr Ser Asp
50 55 60

Ala Thr Tyr Thr Ala Phe His Val Trp Asn Gly Asn Ala Phe Arg Leu
65 70 75 80

Gly Asp His Ile Glu Arg Leu Phe Ser Asn Ala Glu Ser Ile Arg Leu
85 90 95

Ile Pro Pro Leu Thr Gln Asp Glu Val Lys Glu Ile Ala Leu Glu Leu
100 105 110

Val Ala Lys Thr Glu Leu Arg Glu Ala Met Val Trp Val Ala Ile Thr
115 120 125

Arg Gly Tyr Ser Ser Thr Pro Leu Glu Arg Asp Val Thr Lys His Arg
130 135 140

Pro Gln Val Tyr Met Tyr Ala Val Pro Tyr Gln Trp Ile Val Pro Phe
145 150 155 160

Asp Arg Ile Arg Asp Gly Val His Leu Met Val Ala Gln Ser Val Arg
165 170 175

Arg Thr Pro Arg Ser Ser Ile Asp Pro Gln Val Lys Asn Phe Ala Ala
180 185 190

Gly Asp Leu Ile Arg Ala Ile Gln Glu Thr His Asp Arg Gly Phe Glu
195 200 205

Leu Pro Leu Leu Leu Asp His Asp Asn Leu Leu Ala Glu Gly Pro Gly
210 215 220

Phe Asn Val Val Val Ile Lys Asp Gly Val Val Arg Ser Pro Gly Arg
225 230 235 240

Ala Ala Leu Pro Gly Ile Thr Arg Lys Thr Val Leu Glu Ile Ala Arg
245 250 255

Ser Leu Gly His Glu Ala Ile Leu Ala Asp Ile Thr Pro Ala Glu Leu
260 265 270

Arg Asp Ala Asp Glu Val Leu Gly Cys Ser Thr Ala Gly Gly Val Trp
275 280 285

Pro Phe Val Ser Val Asp Gly Asn Ser Ile Ser Asp Gly Val Pro Gly
290 295 300

Pro Val Thr Gln Ser Ile Ile Arg Arg Tyr Trp Glu Leu Asn Val Glu
305 310 315 320

Pro Ser Cys Leu Leu Thr Pro Val Gln Tyr
325 330

SYNTHESIS OF BTK INHIBITOR AND INTERMEDIATES THEREOF

CROSS-REFERENCE TO RELATED APPLICATIONS

This application is a National Stage application of International Patent Application No. PCT/US2022/030997 filed May 26, 2022, which claims the benefit of U.S. provisional patent application No. 63/336,367, filed Apr. 29, 2022, U.S. provisional patent application No. 63/223,693, filed Jul. 20, 2021, and U.S. provisional patent application No. 63/194,307, filed May 28, 2021, each of which is incorporated by reference in its entirety herein.

SEQUENCE LISTING

The instant application contains a Sequence Listing which has been submitted electronically in ASCII format and is hereby incorporated by reference in its entirety. Said ASCII copy, created on May 25, 2022, is named 25247-WO-PCT_SL.txt and is 24,009 bytes in size.

FIELD OF THE INVENTION

The present invention relates to efficient synthetic processes useful in the preparation of Compound A, a BTK inhibitor of Formula (I):

(I)

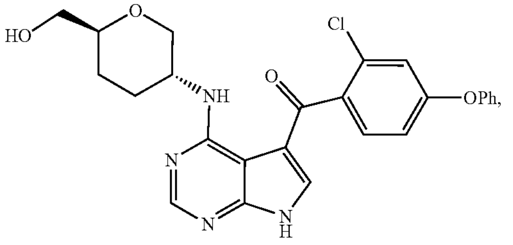

or a pharmaceutically acceptable salt thereof, including the preparation of intermediates used to make Compound A or a pharmaceutically acceptable salt thereof.

BACKGROUND OF THE INVENTION

Bruton's Tyrosine Kinase (BTK) is a member of the Tec family of tyrosine kinases and plays an important role in the regulation of early B-cell development and mature B-cell activation and survival. Functioning downstream of multiple receptors, such as growth factors, B-cell antigen, chemokine, and innate immune receptors, BTK initiates a number of cellular processes including cell proliferation, survival, differentiation, motility, angiogenesis, cytokine production, and antigen presentation.

BTK-deficient mouse models have shown the role BTK plays in allergic disorders and/or autoimmune disease and/or inflammatory disease. Expression of BTK in osteoclasts, mast cells and monocytes has been shown to be important for the function of these cells. For example, impaired IgE-mediated mast cell activation and reduced TNF-alpha production by activated monocytes has been associated with BTK deficiency in mice and humans.

Inhibition of BTK with small molecule inhibitors therefore offers a treatment for hematologic malignancies, immune disorders, cancer, cardiovascular diseases, viral infections, inflammation, metabolism/endocrine function disorders, and neurological disorders. While Compound A can be used to treat diseases or disorders, such as hematological malignancies, existing routes to make Compound A require a multiple step process. In particular, known syntheses of key intermediate 4',

4'

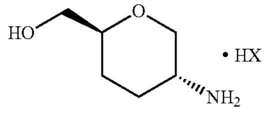

(3R,6S)-6-(Hydroxymethyl)oxan-3-amininium salts, including the free base, from carbohydrate starting materials (N. M. A. J. Kriek et al. Eur. J. Org. Chem. (2003) 2003(13): 2418-27; C. E. Lünse et al. ACS Chem. Biol. (2011) 6(7): 675-78; F. Amann et al. Org. Process Res. Dev. (2016) 20(2): 446-51) or L-serine (J.-C. Gauvin et al. Patent Number WO 2007/105154 A2, and M. J. Dunn et al. J. Org. Chem. (1995) 60(7): 2210-15) are inefficient and complex, as multiple synthetic steps, including several protecting group manipulations, are required. In light of the difficult and lengthy synthetic options developed to date to produce Compound 4', a need exists for synthetic route that minimizes the number of synthetic steps as well as the use of protecting groups to prepare Compound 4' in order to access Compound A in a more sustainable manner.

SUMMARY OF THE INVENTION

The present invention relates to processes useful in the synthesis of Compound A

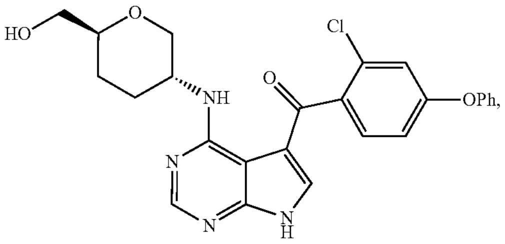 [SMILES: O=C(c1ccc(Oc2ccccc2)cc1Cl)c1c[nH]c2ncnc(N[C@@H]3CC[C@@H](CO)OC3)c12]

or a pharmaceutically acceptable salt thereof, including preparation of intermediates used to make Compound A. The processes of the present invention afford advantages over previously known procedures and include a more efficient route for preparing intermediates useful in the preparation of Compound A.

Other embodiments, aspects and features of the present invention are either further described in or will be apparent from the ensuing description, examples and appended claims.

DETAILED DESCRIPTION OF THE INVENTION

The present disclosure provides enzymatic processes for preparing intermediates used in the manufacturing of Compound A, or a pharmaceutically acceptable salt thereof.

In a first embodiment of the instant invention, a process for preparing Compound 3

3

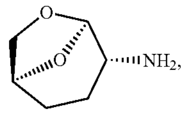

or a pharmaceutically acceptable salt thereof, comprises the steps of:

a) combining a co-factor in a buffer solution or water with isopropylamine and a transaminase enzyme to produce a reagent mixture; and b) adding Compound 2

2

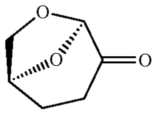

to the reagent mixture to produce a solution comprising Compound 3.

In a further aspect of the first embodiment, the invention relates to the process for preparing Compound 3 comprising the further step of, after adding compound 2 in step c) above heating the solution to about 25° C. to about 70° C. to produce a solution comprising Compound 3.

In a further aspect of the first embodiment, the buffer solution is aqueous sodium tetraborate with a pH of about 6 to about 12.

In a further aspect of the first embodiment, the invention relates to the process for preparing Compound 3 comprising, in step b above, after adding Compound 2, maintaining the pH between about 7 and about 9 by adding an inorganic base to produce a solution comprising Compound 3.

In a further aspect of the first embodiment, the process for preparing compound 3 comprises the further step of, after adding compound 2 in step (c) above, removing the acetone by-product produced in the process by applying vacuum or a nitrogen sweep to produce a solution comprising Compound 3.

In a second embodiment, the invention relates to the process for preparing Compound 3'

3'

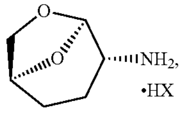

wherein HX is a pharmaceutically acceptable acid comprising the steps of:

a) adding an inorganic base to adjust the pH of a solution comprising Compound 3 to about 12 to about 14;

b) adding a solvent and an inorganic salt to produce a biphasic resulting mixture comprising Compound 3, said biphasic resulting mixture comprising an organic layer and an aqueous layer;

c) separating the organic layer from the biphasic resulting mixture with a solvent;

d) combining the organic layers of the biphasic resulting mixture with a solution of an acid in a solvent, to produce a slurry comprising Compound 3'; and e) filtering the slurry to obtain compound 3' as a solid.

In a further aspect of the second embodiment, the invention relates to the process for preparing Compound 3' further comprising the step of filtering the biphasic resulting mixture of step (b) above to remove the transaminase enzyme.

In a further aspect of the second embodiment, the invention relates to the process for preparing Compound 3' further comprising the steps of:

a) after separating the organic layer in step (c) above, removing isopropylamine by concentrating organic layers to produce a resulting solution comprising Compound 3; and b) combining the resulting solution of Compound 3 with a solution of an acid in a solvent to produce a slurry comprising Compound 3'.

In a further aspect of the second embodiment, the invention relates to the process for preparing Compound 3' comprising the further step of adding water to the organic layers comprising Compound 3 to adjust the water content to about 0 to about the water saturation point of the organic layers before adding a solution of the acid in a solvent in step d) above.

In a further aspect of the second embodiment, the invention relates to a process for preparing Compound 3' wherein HX is a pharmaceutically acceptable acid selected from p-toluene sulfonic acid, benzenesulfonic acid or hydrochloric acid.

In a further aspect of the second embodiment, HX is p-toluenesulfonic acid and Compound 3' is represented as Compound 3a 3a

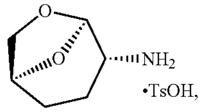

and the process for preparing Compound 3a further comprises the steps of:

a) combining a solution of p-toluenesulfonic acid in a solvent with the organic layers of the resulting biphasic mixture to produce a slurry comprising 3a; and b) filtering the slurry to obtain 3a as a solid.

In a third embodiment, the invention relates to the process for preparing Compound 3' comprising the steps of:

a) adding an inorganic base to adjust the pH of a solution comprising Compound 3 to about 12 to about 14;

b) distilling the solution comprising Compound 3' to remove isopropylamine;

c) adding a base and a solution of di-tert-butyl dicarbonate in a solvent to produce a biphasic resulting mixture comprising Compound 3c 3c

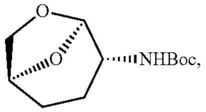

said biphasic resulting mixture comprising an aqueous layer and an organic layer;

d) separating the organic layer of the biphasic resulting mixture comprising Compound 3c by adding a solvent;

e) adding a solution of an acid in a solvent to the organic layer to produce a slurry comprising Compound 3'; and f) filtering the slurry to obtain compound 3' as a solid.

In a further aspect of the third embodiment, the invention relates to the process for preparing Compound 3' comprising the further step of filtering the biphasic resulting mixture comprising Compound 3c, which is produced in step (c) above, to remove the transaminase enzyme.

In a further aspect of the third embodiment, Compound 3' is Compound 3a, and the process for preparing Compound 3a further comprises the steps of:

a) adding a solution of p-toluenesulfonic acid in a solvent to the organic layer comprising Compound 3c in step e) above to produce a slurry comprising Compound 3a; and b) filtering the slurry to obtain Compound 3a as a solid.

In a fourth embodiment of the instant invention, the process for preparing Compound 3' comprises the steps of:

a) combining a transaminase enzyme with a buffer solution or water, and a solid support, followed by incubation to prepare an immobilized transaminase enzyme;

b) washing the immobilized transaminase enzyme with a buffer solution or water;

c) washing with a transamination solvent;

d) combining Compound 2 with isopropylamine and transamination solvent to provide a reaction stream;

e) combining the reaction stream with the immobilized transaminase enzyme to produce a slurry comprising Compound 3;

f) separating the slurry comprising Compound 3 from the immobilized transaminase enzyme to produce a solution comprising Compound 3;

g) combining the solution comprising Compound 3 with a solution of an acid in a transamination solvent to produce a slurry comprising Compound 3'; and h) filtering the slurry to obtain Compound 3' as a solid.

In a further aspect of the fourth embodiment, the process for preparing Compound 3' further comprises combining a co-factor with the transaminase enzyme and the buffer solution to produce a transaminase mixture in step (a) above.

In a further aspect of the fourth embodiment, the buffer solution in step (a) above is a buffer with a pH of about 4 to about 11.

In a further aspect of the fourth embodiment, the buffer solution is aqueous potassium phosphate, and the pH of the buffer from about 6 to about 8.

In a further aspect of the fourth embodiment, water is used in step b) above to wash the immobilized transaminase enzyme in step (b).

In a further aspect of the fourth embodiment, the process for preparing Compound 3' further comprises the step of, washing the immobilized transaminase enzyme with water and then washing the immobilized transaminase enzyme with an isopropanol:PEG-400:water mixture.

In a further aspect of the fourth embodiment, the process for preparing Compound 3' is as described above, wherein the transamination solvent in step c) above is a water-containing transamination solvent.

In a further aspect of the fourth embodiment, the process for preparing Compound 3' further comprises the step of drying the immobilized transaminase enzyme before combining it with the reaction stream.

In a further aspect of the fourth embodiment, the process for preparing Compound 3' further comprises the step of combining Compound 2 with isopropylamine in a water-containing transamination solvent to prepare the reaction stream in step (d) above.

In a further aspect of the fourth embodiment, the process for preparing Compound 3' further comprises the step of, after combining the reaction stream with the immobilized transamination enzyme in step e) above, heating the solution to about 25° C. to about 70° C. to produce a slurry comprising Compound 3.

In a further aspect of the fourth embodiment, the immobilized transaminase enzyme can be reused with a new reaction stream comprising compound 2 to produce a slurry comprising compound 3.

In a further aspect of the fourth embodiment, the process for preparing Compound 3' comprises performing the steps b), c) and e) above in a continuous reaction system wherein the buffer solution or water, the transamination solvent and the reaction stream are continuously passed over the immobilized transaminase enzyme.

In a further aspect of the fourth embodiment, the process for preparing Compound 3' comprises the steps of a) combining the transaminase enzyme with a buffer solution or water to generate a solution comprising the transaminase enzyme;

b) combining the solution comprising the transaminase enzyme with a solid support in a continuous reaction system wherein the solution is continuously passed over the solid support to generate the immobilized transaminase enzyme; and c) performing the steps b) c) and e) of the fourth embodiment in a continuous reaction system wherein the buffer solution or water, the transamination solvent and the reaction stream are continuously passed over the immobilized transaminase enzyme.

In a further aspect of the fourth embodiment, the continuous reaction system is a packed-bed reactor (PBR).

In a further aspect of the fourth embodiment, the process for preparing Compound 3' further comprises the step of distilling the solution comprising compound 3 to remove isopropylamine.

In a further aspect of the fourth embodiment, the invention relates to the process for preparing Compound 3' comprising the further steps of:

a) distilling the solution comprising compound 3 to remove isopropylamine to produce a resulting solution comprising compound 3; and b) adding water to the resulting solution comprising compound 3 to adjust the water content to about 0 to about the water saturation point of the transamination solvent.

In a further aspect of the fourth embodiment, Compound 3' is Compound 3a, and the process for preparing compound 3a further comprises the step of a) combining the solution comprising Compound 3 with a solution of p-toluenesulfonic acid in a transamination solvent to produce a slurry comprising Compound 3a; and b) filtering the slurry to isolated 3a as a solid.

In a further aspect of the fourth embodiment, Compound 3' is Compound 3b, and the process for preparing Compound 3b further comprises the steps of:

a) combining the solution comprising Compound 3 with hydrochloric acid to produce a slurry comprising Compound 3b; and b) filtering the slurry to isolate 3b as a solid.

In a fifth embodiment of the invention, the process for preparing Compound 4'

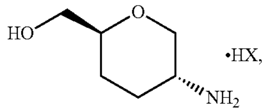

4' wherein HX is a pharmaceutically acceptable acid, comprises the steps of:

a) adding Compound 3' to a weakly coordinating solvent;

b) adding a silane reductant or a borane reductant, and a Lewis acid and heating to about 30° C. to about 70° C. to produce a resulting solution;

c) adding an alcohol to produce a solution comprising Compound 4';

d) cooling the solution to produce a slurry comprising Compound 4'; and e) filtering the slurry to obtain Compound 4' as a solid.

In a further aspect of the fifth embodiment, Compound 4' is Compound 4a

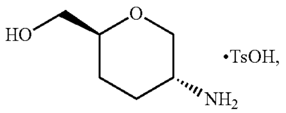

4a and the process for preparing compound 4a further comprises the step of adding Compound 3a to a weakly coordinating solvent in step a) above.

In a further aspect of the fifth embodiment of this invention, the weakly coordinating solvent in step a) above is a mixture of anisole and sulfolane.

In a further aspect of the fifth embodiment, 2,3-dihydrothiophene 1,1-dioxide, also known as 2-sulfolene, or 2,5-dihydrothiophene 1,1-dioxide, also known as 3-sulfolene, are added in step a) above.

In a further aspect of the fifth embodiment of this invention, the silane reductant in step b) above is triethyl silane and the Lewis acid in step b) above is boron trifluoride diethyl etherate, and the ratio of triethyl silane to boron trifluoride diethyl etherate is less than 3:1.

In a further aspect of the fifth embodiment, an antisolvent is added in step d) above to obtain a slurry comprising Compound 4'.

In a further aspect of the fifth embodiment of this invention, the process for preparing Compound 4a is performed in a sealed reactor or a reactor capable of controlling reaction pressure. In a further aspect of the fifth embodiment, the process for preparing Compound 4a, in step b), comprises adding triethyl silane and boron trifluoride diethyl etherate and heating in a reactor to about 30 to about 70° C. to produce a resulting solution, wherein said reactor is a sealed reactor or in a reactor capable of controlling the reaction pressure.

In a sixth embodiment of the invention, the process for preparing Compound 4b

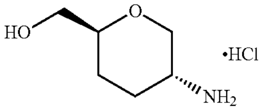

4b comprises the steps of:

a) adding Compound 3a to a weakly coordinating solvent;

b) adding a silane reductant and a Lewis Acid and heating to about 30° C. to about 70° C. to produce a resulting solution;

c) adding an alcohol to produce a solution comprising Compound 4a;

d) adding a solution of hydrochloric acid to produce a slurry comprising Compound 4a; and e) filtering the slurry to obtain Compound 4b as a solid.

In a seventh embodiment of the instant invention, the process for preparing Compound 4b comprises the steps of:

a) adding Compound 3' to an organic solvent;

b) adding an organic base to produce a reaction mixture;

c) adding a silane reductant and trimethylsilyl trifluoromethanesulfonate to the reaction mixture to produce a resulting solution;

d) adding water to the resulting solution to create a two-layer mixture comprising Compound 4b, said two-layer mixture having a top layer and a bottom layer, and separating the bottom phase from the two-layer mixture;

e) cooling the bottom phase to produce a resulting slurry; and f) filtering the slurry to obtain Compound 4b as a solid.

In a further aspect of the seventh embodiment for the preparation of Compound 4b, the silane reductant is chlorodimethylsilane.

In a further aspect of the seventh embodiment Compound 3' is Compound 3a, and the process for preparing Compound 4b further comprises the step of adding Compound 3a to an organic solvent in step a) above.

In a further aspect of the seventh embodiment, an antisolvent is added in step (e) above to obtain a slurry comprising compound 4b.

In an eighth embodiment of the instant invention, the invention relates to a process for preparing Compound 7

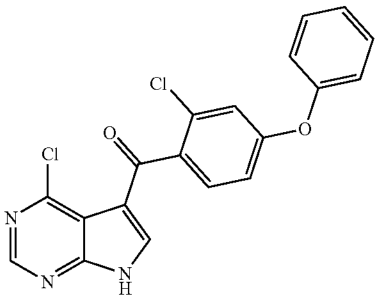

7 comprising the steps of:

a) adding a solution of a first base to a slurry of Compound 5

5

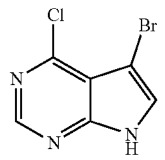

5 in a first aprotic solvent to produce a resulting mixture;

b) combining a solution of a second base with the resulting mixture;

c) adding a solution of Compound 6

6

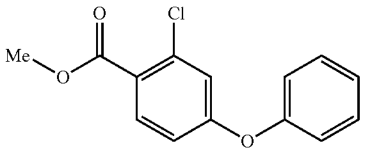

in a second aprotic solvent to produce a solution comprising Compound 7;

d) combining an aqueous solution with the solution comprising Compound 7 to produce a biphasic mixture comprising Compound 7, said biphasic mixture comprising an aqueous layer and an organic layer;

e) separating the organic layer from the biphasic mixture comprising Compound 7;

f) adding an alcohol, water or an alcohol-water mixture to the organic layer to produce a resulting slurry comprising Compound 7; and g) filtering the slurry to obtain Compound 7 as a solid.

In a further aspect of the eighth embodiment, the process for preparing compound 7 comprises the further step of adding lithium bromide in step (a) above.

In a further aspect of the eighth embodiment, the process for preparing compound 7 comprises the further step of combining the resulting mixture with the second base and a solution of Compound 6 in a continuous stirred tank reactor.

In a further aspect of the eighth embodiment, the process for preparing compound 7 comprises the further steps of:

a) adding a solution of a first base to a solution of Compound 5 and lithium bromide in a first aprotic solvent to produce the resulting mixture; and b) combining the resulting mixture with 1) a solution of the second base and 2) a solution of compound 6 in a second aprotic solvent in a plug flow reactor (PFR) to produce a solution comprising Compound 7.

In a further aspect of the eighth embodiment, the process for preparing Compound 7 comprises the further step of treating the organic layer from the biphasic mixture with activated carbon; and then filtering the mixture.

In a further aspect of the eighth embodiment the process for preparing Compound 7 further comprises the step of distilling the organic layer prior to performing step f) above.

In a ninth embodiment of the instant invention, the process for preparing Compound A,

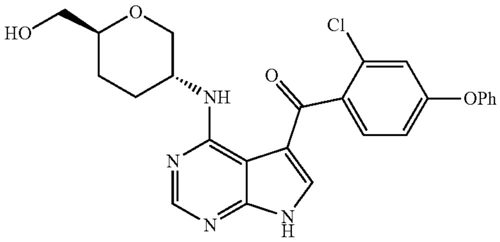 [SMILES: O=C(c1ccc(Oc2ccccc2)cc1Cl)c1c[nH]c2ncnc(N[C@@H]3CC[C@@H](CO)OC3)c12]

or a pharmaceutically acceptable salt thereof, comprises the steps of:

a) adding a base to a slurry comprising a mixture of compound 7

7

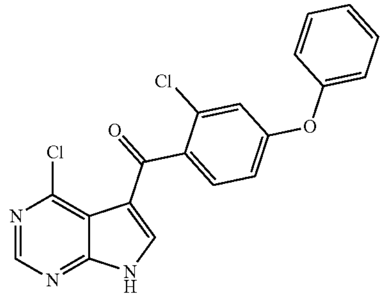

and compound 4',

4'

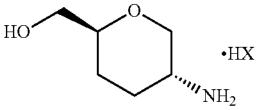

wherein HX is a pharmaceutically acceptable acid thereof, in a reaction solvent to produce a resulting mixture;

b) heating the resulting mixture to produce a solution comprising Compound A;

c) adding a crystallization solvent to produce a slurry comprising Compound A; and d) filtering the slurry to obtain Compound A as a solid.

In a further aspect of the ninth embodiment, the process for preparing Compound A comprises the step of using Compound 4a 4a

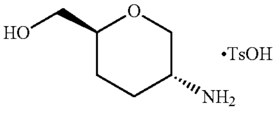

in step a) above.

In a further aspect of the ninth embodiment, the process for preparing compound A further comprises the step of using N,N-diisopropylethylamine (DIPEA) as the base.

In a further aspect of the ninth embodiment, the process for preparing Compound A comprises the step of heating the resulting mixture of step (a) above to about 40 to about 85° C. to produce a solution comprising Compound A.

In a further aspect of the ninth embodiment, the process for preparing Compound A comprises the further steps of:

a) adding water as the crystallization solvent to produce a slurry comprising Compound A;

b) cooling the slurry and adding acetic acid to adjust the pH to about 11 to about 4; and c) filtering the slurry to obtain Compound A as a solid.

In the embodiments of the instant invention, the processes of the disclosure may be conducted in a single vessel, as a "one-pot" process, or the steps may be conducted sequentially. For clarity, it should be noted that steps and reactions of the instant invention may occur simultaneously, or sequentially, unless otherwise specifically designated. In embodiments, the intermediate products may optionally be isolated. It should also be noted that when a term is used more than once, such as organic solvent, the definition at each instance is independent of a prior selection. For example, the same, or a different, organic solvent may be chosen for each step of the process independently of a previous selection.

Definitions

Certain technical and scientific terms are specifically defined below. Unless specifically defined elsewhere in this document, all other technical and scientific terms used herein have the meaning commonly understood by one of ordinary skill in the art to which this disclosure relates. That is, terms used herein have their ordinary meaning, which is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated.

Any example(s) following the term "e.g." or "for example" is not meant to be exhaustive or limiting.

As used herein, and throughout this disclosure, the following terms, unless otherwise indicated, shall be understood to have the following meanings:

As used herein, the expressions "compound of Formula (I)", "Compound (I)", and "Compound A" refer to the same compound and can be used interchangeably.

As used herein, including the appended claims, the singular forms of words such as "a." "an," and "the," include their corresponding plural references unless the context clearly dictates otherwise.

As used herein, the terms "at least one" item or "one or more" item each include a single item selected from the list as well as mixtures of two or more items selected from the list.

Unless expressly stated to the contrary, all ranges cited herein are inclusive; i.e., the range includes the values for the upper and lower limits of the range as well as all values in between. All ranges also are intended to include all included sub-ranges, although not necessarily explicitly set forth. As an example, temperature ranges, percentages, ranges of equivalents, and the like described herein include the upper and lower limits of the range and any value in the continuum there between. Numerical values provided herein, and the use of the term "about", may include variations of ±1%, ±2%, ±3%, ±4%, ±5%, and ±10% and their numerical equivalents. "About" when used to modify a numerically defined parameter (e.g., the temperature, or the length of time for a reaction, as described herein) means that the parameter may vary by as much as 10% below or above the stated numerical value for that parameter; where appropriate, the stated parameter may be rounded to the nearest whole number. For example, a temperature of about 30° C. may vary between 25° C. and 35° C. In addition, the term "or," as used herein, denotes alternatives that may, where appropriate, be combined; that is, the term "or" includes each listed alternative separately.

As used herein, Compound 2 may also be referred to herein as Cyrene or (1S,5R)-6,8-Dioxabicyclo[3.2.1]octan-4-one. Compound 3 may also be referred to herein as 1S,4R,5R)-6,8-Dioxabicyclo[3.2.1]octan-4-amine. Compound 3a may also be referred to herein as (1S,4R,5R)-6,8-Dioxabicyclo[3.2.1]octan-4-aminium 4-methylbenzene-1-sulfonate. Compound 3b may also be referred to herein as (1S,4R,5R)-6,8-Dioxabicyclo[3.2.1]octan-4-aminium hydrochloride. Compound 4a may also be referred to herein as (3R,6S)-6-(Hydroxymethyl)oxan-3-aminium 4-methylbenzene-1-sulfonate. Compound 4b may also be referred to herein as (3R,6S)-6-(Hydroxymethyl)oxan-3-aminium hydrochloride. Compound 5 may also be referred to herein as 5-Bromo-4-chloro-7H-pyrrolo[2,3-d]pyrimidine. Compound 6 may also be referred to herein as Methyl 2-chloro-4-phenoxybenzoate. Compound 7 may also be referred to herein as (2-Chloro-4-phenoxyphenyl)(4-chloro-7H-pyrrolo[2,3-d]pyrimidin-5-yl)methanone. The compound of the formula I. Compound A may also be referred to herein as (2-Chloro-4-phenoxyphenyl)(4-{[(3R,6S)-6-(hydroxymethyl)oxan-3-yl]amino}-7H-pyrrolo[2,3-d]pyrimidin-5-yl)methanone.

For use in medicine, the salts of the compounds described herein will be pharmaceutically acceptable salts. Other salts may, however, be useful in the preparation of the compounds or their pharmaceutically acceptable salts, according to the invention. When the compound of the present invention is acidic, suitable "pharmaceutically acceptable salts" refers to salts prepared from pharmaceutically acceptable non-toxic bases including inorganic bases and organic bases. Examples of inorganic bases include aluminum, ammonium, calcium, copper, ferric, ferrous, lithium, magnesium, manganic salts, manganous, potassium, sodium, zinc and similar salts. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline. $N,N^1$-dibenzylethylenediamine, diethylamine. 2-diethylaminoethanol. 2-dimethylaminoethanol, ethanolamine, ethylenediamine. N-ethylmorpholine. N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Additional examples of such acids include aryl sulfonic acids, such as but not limited to p-toluenesulfonic acid. 3-methyl-toluenesulfonic acid. 2-methyl-toluenesulfonic acid, benzenesulfonic acid. 2-naphthalene sulfonic acid. 2,6-naphtalene sulfonic acid, as well as hydrochloric acid, hydrobromic acid, sulfuric acid, acetic acid, phenyl acetic acid, trimethylacetic acid, tetrafluoroboric acid, tetraphenylboric acid, maleic acid, fumaric acid, oxalic acid, or camphorsulfonic acid. Specific examples are citric, hydrobromic, p-toluenesulfonic, benzenesulfonic, hydrochloric, maleic, phosphoric, sulfuric and tartaric acids. Preferred are p-toluenesulfonic, benzenesulfonic, and hydrochloric acids.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

One or more compounds herein may exist in unsolvated as well as solvated forms with pharmaceutically acceptable solvents, such as water, ethanol, and the like, and this disclosure is intended to embrace both solvated and unsolvated forms. "Solvate" means a physical association of a compound with one or more solvent molecules. This physical association involves varying degrees of ionic and covalent bonding, including hydrogen bonding. In certain instances of this aspect, the solvate will be capable of isolation, for example when one or more solvent molecules are incorporated in the crystal lattice of a crystalline solid. "Solvate" encompasses both solution-phase and isolatable solvates. Non-limiting examples of suitable solvates include ethanolates, methanolates, and the like. "Hydrate" is a solvate in which the solvent molecule is $H_2O$.

The present disclosure further includes compounds and synthetic intermediates in all their isolated forms. For example, the identified compounds are intended to encompass all forms of the compounds such as, any solvates, hydrates, stereoisomers, and tautomers thereof.

Those skilled in the art will recognize that certain compounds, and in particular compounds containing certain heteroatoms and double or triple bonds, can be tautomers, structural isomers that readily interconvert. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-imine. (Pyrrolopyrimidinyl)methanone-(Pyrrolopyrimidinyl)methanol tautomeric pairs are included in the present application:

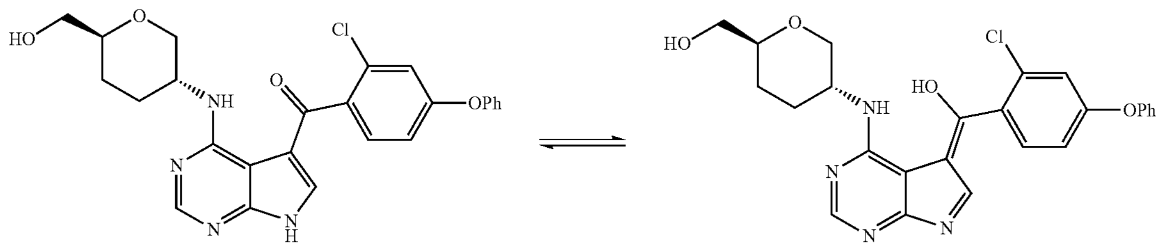

(pyrrolo[2,3-d]pyrimidinyl)methanone (pyrrolo[2,3-d]pyrimidinylidene)methanol

Those skilled in the art will recognize that chiral compounds, such as the compounds presented herein, can be drawn in a number of different ways that are equivalent.

The term "alkyl" refers to a straight or branched hydrocarbon chain radical consisting solely of carbon and hydrogen atoms, containing no unsaturation. Alkyl may contain one to ten carbon atoms (e.g., $C_1$-$C_{10}$ alkyl), unless otherwise stated. In other embodiments, an alkyl comprises one to eight carbon atoms (e.g., $C_1$-$C_8$ alkyl). In other embodiments, an alkyl comprises one to four carbon atoms (e.g., $C_1$-$C_6$ alkyl). In other embodiments, the alkyl group is selected from methyl, ethyl, propyl, butyl or pentyl. In other embodiments, the alkyl group is selected from methyl, ethyl, 1-propyl (n-propyl), 1-methylethyl (iso-propyl), I-butyl (n-butyl), 1-methylpropyl (sec-butyl), 2-methylpropyl (isobutyl), 1,1-dimethylethyl (tert-butyl), or 1-pentyl (n-pentyl). In other embodiments, the alkyl group is selected from methyl, ethyl, -propyl or butyl. In other embodiments, the alkyl is methyl.

As used herein, term "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl. In an embodiment of the instant invention, aryl is phenyl or naphthyl. In an embodiment, aryl is phenyl.

As used herein, the term co-factor refers to a non-protein compound that operates in combination with a transaminase enzyme. Co-factors suitable for use with the engineered transaminase enzymes described herein include compounds from the vitamin B6 family, such as, but not limited to pyridoxal 5'-phosphate (PLP) or pyridoxamine 5'-phosphate (PMP). In some embodiments, the co-factor is pyridoxal 5'-phosphate monohydrate.

As used herein, a buffer solution refers to a solution which, when added to a liquid mixture, functions to maintain the pH of the liquid mixture at a consistent value. In embodiments of the invention, the buffer solution is independently selected from aqueous sodium tetraborate, aqueous tris(hydroxymethyl)aminomethane ("tris"), aqueous bis(2-hydroxyethyl)amino-tris(hydroxymethyl)methane ("bis-tris"), aqueous triethanolamine (TEOA), aqueous potassium phosphate, aqueous 4-(2-hydroxyethyl)-1-piperazineethanesulfonic acid (HEPES), or aqueous 2-[[1,3-dihydroxy-2-(hydroxymethyl)propan-2-yl]amino]ethanesulfonic acid (TES). In further embodiments, the buffer solution is independently selected from aqueous sodium tetraborate or aqueous potassium phosphate.

The transaminase enzymes described herein are the product of directed evolution from a commercially available transaminase, Enzyme 1, shown as SEQ ID NO: 1 herein (described in Yasuda, N.; Cleator, E.; Kosjek, B.; Yin, J.; Xiang, B. et al. *Org. Process Res. Dev.* 2017, 21, 1851-1858; PCT Publications WO2010/099501 and WO2013/036861 and U.S. Pat. No. 9,109,209.) Enzyme 1 (SEQ ID NO:1) is commercially available as lyophilized cell-free lysate from Codexis, Inc., Redwood City, California. Transaminases enzymes are capable of catalyzing the stereoselective reduction of ketones to amines. As used herein, the transaminase enzymes may be lyophilized cell-free lysates, crude lysates, whole cell proteins, cell-free lysates or purified enzymes.

In the embodiments, the transaminase enzymes described herein have amino acid sequences that may have one or more amino acid differences, as compared to a reference transaminase amino acid sequence (Enzyme 1—SEQ ID NO: 1). The transaminase enzymes used in the instant invention have amino acid sequences that have substantial identity to SEQ ID NO: 1. In some embodiments, the transaminase enzymes have amino acid sequences that have an 90% or greater sequence identity with SEQ ID NO: 1. The transaminase enzymes described herein include, but are not limited to, those of Enzyme 1, 2, 3, 4, 5, 6, 7, or 8, having SEQ ID NO: 1, 2, 3, 4, 5, 6, 7 or 8 respectively. Enzyme 2 through Enzyme 8 are described in a separate, commonly owned patent application, co-filed on the same day, incorporated by reference herein in its entirety.

Additional examples of transaminase enzymes useful in the instant invention are also described in PCT Publications WO2010/099501, WO2012024104 and WO2013036861, particularly SEQ ID NO: 74 and 102 from WO 2010/099501 and SEQ ID NO: 206 from WO2012/024104, as well as others covered by the publications. In some embodiments of the invention, the transaminase enzyme is selected from Enzyme 1 (SEQ ID NO: 1) or Enzyme 6 (SEQ ID NO: 6). In embodiments of the invention, the transaminase enzymes described herein include Enzyme 1 having the amino acid sequence as set forth below in SEQ ID NO: 1

(SEQ ID NO: 1)

MAFSADTPEIVYTHDTGLDYITYSDYELDPANPLAGGAAWIEGAFVPPS

EARISIFDQGFYTSDATYTVFHVWNGNAFRLGDHIERLFSNAESIRLIP

PLTQDEVKEIALELVAKTELREAIVWVAITRGYSSTPLERDVTKHRPQV

YMYAVPYQWIVPFDRIRDGVHLMVAQSVRRTPRSSIDPQVKNFAAGDLI

RAIQETHDRGFELPLLLDFDNLLAEGPGFNVVVIKDGVVRSPGRAALPG

ITRKTVLEIAESLGHEAILADITPAELRDADEVLGCSTAGGVWPFVSVD

GNSISDGVPGPVTQSIIRRYWELNVEPSCLLTPVQY

In embodiments, the transaminase enzymes described herein include transaminase Enzyme 2 having the amino acid sequence as set forth below in SEQ ID NO: 2

SEQ ID NO: 2)

MAFSLDTPEIVYTHDTGLDYITYSDYELDPANPLAGGAAWIEGAFVPPS

EARISIFDQGFYTSDATYTVFHVWNGNAFRLGDHIERLFSNAESIRLIP

PLTQDEVKEIALELVAKTELREAIVWVAITRGYSSTPLERDVTKHRPQV

YMYAVPYQWIVPFDRIRDGVHLMVAQSVRRTPRSSIDPQVKNFAAGDLI

RAIQETHDRGFELPLLLDFDNLLAEGPGFNVVVIKDGVVRSPGRAALPG

ITRKTVLEIAESLGHEAILADITPAELRDADEVLGCSTAGGVWPFVSVD

GNSISDGVPGPVTQSIIRRYWELNVEPSCLLTPVQY

In embodiments, the transaminase enzymes described herein include transaminase Enzyme 3 having the amino acid sequence as set forth below in SEQ ID NO: 3.

(SEQ ID NO: 3)

MAFSLDTPEIVYTHDTGLDYITYSDYELDPANPLAGGAAWIEGAFVPPS

EARISVFDQGFYTSDATYTVFHVWNGNAFRLGDHIERLFSNAESIRLIP

PLTQDEVKEIALELVAKTELREAMVWVAITRGYSSTPLERDVTKHRPQV

YMYAVPYQWIVPFDRIRDGVHLMVAQSVRRTPRSSIDPQVKNFAAGDLI

RAIQETHDRGFELPLLLDHDNLLAEGPGFNVVVIKDGVVRSPGRAALPG

ITRKTVLEIARSLGHEAILADITPAELRDADEVLGCSTAGGVWPFVSVD

GNSISDGVPGPVTQSIIRRYWELNVEPSCLLTPVQY

In embodiments, the transaminase enzymes described herein include transaminase Enzyme 4 having the amino acid sequence as set forth below in SEQ ID NO: 4.

(SEQ ID NO: 4)

MAFSLDTPEIVYTHDTGLDYITYSDYELDPANPLAGGAAWIEGAFVPPS

EARISVFDQGFYTSDATYTVFHVWNGNAFRLGDHIERLFSNAESIRLIP

PLTQDEVKEIALELVAKTELREAMVWVAITRGYSSTPLERDVTKHRPQV

YMYAVPYQWIVPFDRIRDGVHLMVAQSVRRTPRSSIDPQVKNFASIDLI

RAIQETHDRGFELPLLLDHDNLLAEGPGFNVVVIKDGVVRSPGRAALPG

ITRKTVLEIAESLGHEAMLADITPAELRDADEVLGCSTAGGVWPFVSVD

GNSISDGVPGPVTQSIIRRYWELNVEPSCLLTPVQY

In embodiments, the transaminase enzymes described herein include transaminase Enzyme 5 having the amino acid sequence as set forth below in SEQ ID NO: 5.

(SEQ ID NO: 5)

MAFSLDTPEIVYTHDTGLDYITYSDYELDPANPLAGGAAWIEGAFVPPS

EARISVFDQGFYTSDATYTAFHVWNGNAFRLGDHIERLFSNAESIRLIP

PLTQDEVKEIALELVAKTELREAMVWVAITRGYSSTPLERDVTKHRPQV

YMYAVPYQWIVPFDRIRDGVHLMVAQSVRRTPRSSIDPQVKNFASIDLI

RAIQETHDRGFELPLLLDHDNLLAEGPGFNVVVIKDGVVRSPGRAALPG

ITRKTVLEIAESLGHEAMLADITPAELRDADEVLGCSTAGGVWPFVSVD

GNSISDGVPGPVTQSIIRRYWELNVEPSCLLTPVQY

In embodiments, the transaminase enzymes described herein include transaminase Enzyme 6 having the amino acid sequence as set forth below in SEQ ID NO: 6.

(SEQ ID NO: 6)

MAFSLDTPEIVYTHDTGLDYITYSDYELDPANPLAGGAAWIEGAFVPVS

EARISVFDQGFYASDATYTAFHVWNGNAFRLGDHIERLWSNAESIRLIP

PLTQDEVKEIALELVAKTELREAMVGVAITRGYSSTPLERDVTKHRPQV

YMYAVPYQWIVPFDRIRDGVHLMVAQSVRRTPRSSIDPQVKNFASIDLI

RAIQETHDRGFELPLLLDHDNLLAEGPGFNVVVIKDGVVRSPGRAALPG

-continued

ITRKTVLEIARSLGHEAMLADITPAELRDADEVLGCSTAGGVWPFVSVD

GNSISDGVPGPVTQSIIRRYWELNVEPSCLLTPVQY

In embodiments, the transaminase enzymes described herein include transaminase Enzyme 7 having the amino acid sequence as set forth below in SEQ ID NO: 7.

(SEQ ID NO: 7)

MAFSLDTPEIVYTHDTGLDYITYSDYELDPANPLAGGAAWIEGAFVPVS

EARISVFDQGFYASDATYTAFHVWNGNAFRLGDHIERLWSNAESIRLIP

PLTQDEVKEIALELVAKTELREAMVGVVITRGYSSTPLERDVTKHRPQV

YMYAIPYQWIVPFDRIRDGVHLMVAQSVRRTPRSSIDPQVKNFASIDLI

RAIQETHDRGFELPLLLDHDNLLAEGPGFNVVVIKDGVVRSPGRAALPG

ITRKTVLEIARSLGHEAMLADITPAELRDADEVLGCSTAGGVWPFVSVD

GNSISDGVPGPVTQSIIRRYWELNVEPSCLLTPVQY

In embodiments, the transaminase enzymes described herein include transaminase Enzyme 8 having the amino acid sequence as set forth below in SEQ ID NO: 8.

(SEQ ID NO: 8)

MAFSLDTPEIVYTHDTGLDYITYSDYELDPANPLAGGAAWIEGAFVPPS

EARISVFDQGFYTSDATYTAFHVWNGNAFRLGDHIERLFSNAESIRLIP

PLTQDEVKEIALELVAKTELREAMVWVAITRGYSSTPLERDVTKHRPQV

YMYAVPYQWIVPFDRIRDGVHLMVAQSVRRTPRSSIDPQVKNFAAGDLI

RAIQETHDRGFELPLLLDHDNLLAEGPGFNVVVIKDGVVRSPGRAALPG

ITRKTVLEIARSLGHEAILADITPAELRDADEVLGCSTAGGVWPFVSVD

GNSISDGVPGPVTQSIIRRYWELNVEPSCLLTPVQY

In embodiments of the invention, the inorganic base is independently selected from lithium hydroxide, sodium hydroxide, potassium hydroxide, potassium carbonate, sodium carbonate or potassium phosphate. In further embodiments, the inorganic base is independently selected from sodium hydroxide or potassium hydroxide.

In embodiments of the invention, a solvent is independently selected from 2-methyl THF, THF, MTBE, CPME, toluene, anisole, ethyl acetate, isopropyl acetate (IPAc) or $C_5$-$C_{10}$ alkyl alcohols such as n-butanol. In further embodiments, the solvent is selected from 2-methyl THF, MTBE or IPAc. In some embodiments, the solvent is 2-methyl THF.

In some embodiments of the invention, the inorganic salt is selected from potassium carbonate, potassium phosphate, sodium phosphate, sodium carbonate, sodium sulfate, sodium hydroxide or potassium hydroxide. In further embodiments, the inorganic salt is potassium carbonate or potassium phosphate.

In some embodiments of the invention, the acid is independently selected from aryl sulfonic acids such as but not limited to p-toluenesulfonic acid, 3-methyl-toluenesulfonic acid, 2-methyl-toluenesulfonic acid, benzenesulfonic acid, 2-naphthalene sulfonic acid, 2,6-naphtalene sulfonic acid, as well as hydrochloric acid, hydrobromic acid, sulfuric acid, acetic acid, phenyl acetic acid, trimethylacetic acid, tetrafluoroboric acid, tetraphenylboric acid, maleic acid, fumaric acid, oxalic acid, or camphorsulfonic acid. In further embodiments, the acid is independently selected from p-toluenesulfonic acid or hydrochloric acid.

In some embodiments of the invention, hydrochloric acid (in an organic solvent) is independently selected from, but not limited to, hydrochloric acid in 1,4-dioxane, hydrochloric acid in diethyl ether, hydrochloric acid in CPME or 37% aqueous hydrochloric acid. Alternatively, hydrochloric acid may also be prepared in situ in an organic solvent by combining trimethylsilyl chloride or acetyl chloride with methanol or ethanol.

In embodiments of the invention, the base is independently selected from N,N-diisopropylethylamine (DIPEA), triethylamine, DBU, DBN, DABCO, pyridine and pyridine derivatives such as 2,6-lutidine and 2-methylpyridine, sodium hydroxide, potassium hydroxide, potassium carbonate, potassium phosphate, potassium acetate, sodium carbonate or sodium acetate. In some embodiments the base is DIPEA.

As described herein, the term "immobilization" or "immobilized" refers to a covalent or non-covalent interaction between the enzyme and solid support, encapsulation of enzymes within a porous matrix or polymer, crosslinking of enzymes to form an insoluble aggregate, and similar techniques known to those skilled in the art. Such interactions include hydrogen bonding, ionic or electrostatic interactions, hydrophobic interactions, van-der Waals interactions, electrostatic interactions, π-π interactions, hydrophilic interactions, coordinative interactions, biospecific or affinity interactions, covalent interactions, combinations thereof and the like.

The terms "solid support" or "resin" refer to the solid material composition of the immobilization support. The solid material can be organic or inorganic. The physical properties and form of the solid material include, but are not limited to features such as: porosity, shape or morphology, form factor (particle, monolith), bulk density, cross linking density, particle size, pore size, pore size distribution, particle or shape distribution, or other properties which are well known in the art.

When the material for the solid support is inorganic, it is formed as a solid and is comprised of appropriate minerals, ceramics, metals or other inorganic material which are well known in the art. By way of example, inorganic solid materials include but are not limited to: glass, silica, hydroxyapatite, activated aluminas, diamataceous earths (Celite®), magnesium silicate (Florisil®), titanium dioxide, iron oxide, aluminosilicates, mixtures of the like and combinations thereof.

When the material for the solid support is organic, it is formed as a solid and is comprised of appropriate organic polymers which are well known in the art. By way of example, organic solid materials include, but are not limited to: polymethacrylate, polyacrylate, polymethacrylamide, polyvinyl alcohol, polyacrylamide, polystyrene, polypropylene, polydivinylbenzene, polymers formed from vinyl-based monomers, co-polymers of hydroxyethyl methacrylate and divinylbenzene, co-polymers of styrene and divinylbenzene, co-polymers of acrylamido and vinylic monomers, co-polymers of methacrylate and divinylbenzene, co-polymers of phenol-formaldehyde, agarose, chitosan, cellulose, dextran, activated carbons, mixtures of the like and combinations thereof.

In other instances, the solid support material composition may contain combinations of both organic and inorganic components and it is formed as a solid comprised of inorganic and organic material which are well known in the art. By way of example, such materials include, but are not limited to: glass, silica, hydroxyapatite, activated aluminas, diamataceous earths (Celite®), magnesium silicate (Florisil®), titanium dioxide, iron oxide, aluminosilicates, polymethacrylate, polyacrylate, polymethacrylamide, polyvinyl alcohol, polyacrylamide, polystyrene, polypropylene, polydivinylbenzene, polymers formed from vinyl-based monomers, co-polymers of hydroxyethyl methacrylate and divinylbenzene, co-polymers of styrene and divinylbenzene, co-polymers of acrylamido and vinylic monomers, co-polymers of methacrylate and divinylbenzene, co-polymers of phenol-formaldehyde, agarose, cellulose, dextran, activated carbons, mixtures of the like and combinations thereof.

The composition of the solid support may contain zero, one or more additional reactive species or ligands which impart identical or differential functionality to the resin surface to facilitate covalent or non-covalent interactions between the enzyme and the resin. By way of example, reactive species or ligands include, but are not limited to at least one functional group selected from the group consisting of: strong ion exchangers, weak ion exchangers, multimodal ligands, modifiers, and hydrophobic modifiers, and mixtures thereof. In more specific examples, at least one ligand is selected from the group consisting of amine, quaternary ammonium, sulphonic acid, carboxylic acid, sulfopropyl, methyl sulfonate, diethylaminoethyl, carboxymethyl, hexylamine, ethylamine, iminodiacetic acid, nitrilotriacetic acid, tris carboxymethyl ethylene diamine. (C1-C8)alkyl, octadecyl, $(C_{30})$alkyl, butyldimethyl, biphenyl, pentafluoropropyl, cyanopropyl, aminopropyl, aryl, biotin, desthiobiotin, thiol, amide, alkoxy, acetal, ketal, ester, anhydride, carbonyl, nitrile, epoxy, carboxyamide, ammonium, iodo, phenolic, imidazolyl, morpholinyl, pyridyl, phenyl, sulfide, disulfide, sulfhydryl ketone, acyl chloride, imine, nitrile, anilino, nitro, halo, hydroxyl, maleimide, iodoacetyl, triazine, sulfonate, alkylamine, diol, hydrazide, hydrazine, azlactone, aldehyde, diazonium, carboxylate, azide, vinyl sulfone, epoxide, and oxirane groups, and combinations thereof and the like. In even more specific examples, at least one ligand selected from the previous group is connected to the resin by a homobifunctional or heterobifunctional spacer arm that is included to impart identical or different functionality to the ligands in the previous group. Spacer arms are well known in the art and include but are not limited to $(C_2-C_{20})$alkylene groups that may incorporate one or more hetero atom, aromatic groups, alkylaromatic groups, amido groups, amino groups, urea groups, carbamate groups, ether groups, thio ether groups, and the like and combinations thereof. In even more specific instances, the spacer arm is one or more selected from the group consisting of ethylenediamine, 1,3-diamino-2-propanol, diaminodipropylamine (DADPA), cystamine, 1,6-diaminohexane, O-(2-Aminopropyl)-O'-(2-methoxyethyl) polypropylene glycols such as Jeffamine™ ED-600, unhindered diamines such as Jeffamine™ EDR-148 polyetheramine. 4,7,10-trioxa-1,13-tridecanediamine, Boc-N-amido-$dPEG_{11}$-amine, Boc-N-amido-$dPEG_3$-amine, beta-alanine, aminocaproic acid, amino-$PEG_n$-carboxylate compounds (where n is between 2 and 20), succinic acid, succinic anhydride, glutaric acid, glutaric anhydride, diglycolic acid, diglycolic anhydride, thioglycolic acid. N-succinimidyl S-acetylthioacetate, N-succinimidyl S-acetylthiopropionate, N-acetyl homocysteine thiolactone. 8-mercaptooctanoic acid, alpha-lipoic acid, lipoamide-$PEG_n$-carboxylate compounds (where n is between 2 and 20), thiol-$PEG_n$-carboxylate compounds (where n is between 2 and 20), NHS-$PEG_n$-acetylated thiol compounds, dithiothreitol (DTT) (where n is between 2 and 20), tetra (ethylene glycol) dithiol, hexa(ethylene glycol) dithiol, poly (ethylene glycol) dithiol. 2-mercaptoethylamine, adipic dihydrazide and carbohydrazide.

In one aspect the transaminase enzyme is immobilized on or within a solid support.

In some embodiments the transaminase enzyme is immobilized by non-covalent bonds on a polymeric resin. The polymeric resin may include, but is not limited to, polymethacrylate, polyacrylate, polystyrene-divinylbenzene, or methacrylate-divinylbenzene or the like. The resin may be selected from Diaion® Hp2mgl, Diaion® SP2mgl, Purolite® PAD950, Purolite® ECR1090F, Amberlite® XAD7HP, Chiralvision® IB-ADS-1, Diaion® HP-20 or the like.

In an embodiment the transaminase enzyme is immobilized by non-covalent bonds on a resin that comprises at least one reactive ligand or functional group selected from the group consisting of weak ion exchangers and strong ion exchangers. As described herein, the reactive ligand is selected from the group consisting of: quaternary ammonium groups, ammonium chloride, ammonium hydroxide, triethylammonium groups, dimethylammonium groups, primary amine groups, secondary amine groups, tertiary amine groups, sulfonic acids, carboxylic acids, diethylaminomethyl, carboxymethyl, quaternary ammonium, sulfopropyl, methyl sulfonate, diethylaminoethyl, carboxymethyl, hexylamine, and ethylamine, or linear primary aliphatic amines. In an embodiment, the reactive ligand is selected from the group consisting of: hexylamine or ethylamine. In other instances, the resin is chosen from the group consisting of: Purolite® ECR8304, Purolite® ECR8309, Purolite® ECR8315, Purolite® ECR8404, Purolite® ECR8409, Purolite® ECR8415, Purolite® ECR1508, Resindion® EC-HG, Resindion® EC-EA, Resindion® EC-HA, Resindion® QA, Resindion® HFA113, Resindion® HF A403, Resindion® EA403, Resindion® HA403, Resindion® QA403.

In some embodiments, the transaminase enzyme is immobilized on at least one resin comprising at least one chelating ligand selected from the group consisting of iminodiacetic acid (IDA), nitrilotriacetic acid (NTA), tris carboxymethyl ethylene diamine (TED), and mixtures thereof. In an embodiment, at least one chelating ligand is NTA. In another embodiment, the transaminase enzyme is immobilized on at least one resin comprising at least one chelating ligand, comprising at least one metal ion selected from the group consisting of $Fe^{2+}$, $Cu^{2+}$, $Mg^{2+}$, $Zn^{2+}$, $Co^{2+}$, and $Ni^{2+}$.

In an embodiment the transaminase enzyme is immobilized by non-covalent bonds on a resin that comprises at least one reactive ligand or functional group selected from the group consisting of non-ionizable ligands, ionizable ligands, hydrophobic ligands, hydrophilic ligands, aromatic ligands, heterocyclic groups or combinations thereof. In an embodiment, the exposed ligand comprises a functional group ligand or functional group selected from the group consisting of hydroxyl, hydrocarbyl, methyl, ethyl butyl, octyl, octadecyl, cyanopropyl, pentyl, hexyl, aryl, octadecyl, t-butyl, carboxylic acid, sulfonic acid, amide, alkyl thiol, or amine, pyridyl, imidazolyl or combinations thereof. By way of example, ligands include, but are not limited to: alkylamine, α,ω-Diamino alkane, Phenylalkylamine, 2-Amino-1-phenyl-1,3-propanediol, N-Benzyl-N-methyl ethanol amine, 4-Mercaptoethylpyridine, 2-aminomethylpyridine, mercaptomethylimidazole. 2-Mercaptobenzimidazole, Tryptamine, 5-aminoindole, aminoalkyl carboxyl acid, N-(3-Carboxypropionyl) aminodecyl amine, N-pyromellityl aminodecyl amine, 2-benzamido-4-mercaptobutanoic acid, 2-mercapto-5-benzimidazole sulfonic acid, 6-amino-4-hydroxy-2-naphtalene sulfonic acid, 2,5-dimercapto-1,3,4-thiadiazole, hexylamine, the like and combinations thereof. In other instances, the resin is chosen from the group consisting of: Purolite® ECR8806, Purolite® ECR1030, Resindion® RB1, Resindion® RB2, Resindion® RB3, Resindion® BU113, Resindion® BU114, Resindion® PH400, Resindion® EC-BU, Chiralvision® IB-ADS-4, or the like.

In some embodiments, the transaminase enzyme is immobilized by covalent bonds on at least one resin that includes at least one exposed ligand that can be further reacted. In an embodiment, the exposed ligand comprises a functional group ligand or functional group selected from the group consisting of aryl, biotin, desthiobiotin, thiol, amine, amide, alkoxy, acetal, ketal, ester, anhydride, carbonyl, nitrile, epoxy, carboxyamide, ammonium, iodo, phenolic, imidazolyl, morpholinyl, pyridyl, phenyl, sulfide, disulfide, sulfhydryl ketone, acyl chloride, imine, nitrile, anilino, nitro, halo, alkyl, hydroxyl, maleimide, iodoacetyl, triazine, sulfonate, alkylamine, diol, hydrazide, hydrazine, azlactone, aldehyde, diazonium, carboxylate, azide, vinyl sulfone, epoxide, and oxirane groups, and combinations thereof. In other instances, the resin is chosen from the group consisting of: Chiralvisio® IB-COV-1. Chiralvision® IB-COV-2, Purolite® ECR8204, Resindion® EC-EP, Resindion® EC-HFA, Resindion® HF A403, or the like. In another embodiment, the ligand may be further reacted with a homobifunctional or heterobifunctional spacer arm to impart identical or different functionality. Spacer arms are well known in the art and include but not limited to (C2-C20)alkylene groups that may incorporate one or more hetero atom, aromatic groups, alkylaromatic groups, amido groups, amino groups, urea groups, carbamate groups, ether groups, thio ether groups, and the like and combinations thereof. In an embodiment, the spacer arm is one or more selected from the group consisting of ethylenediamine. 1,3-diamino-2-propanol, diaminodipropylamine (DADPA), cystamine. 1,6-diaminohexane. O-(2-Aminopropyl)-O'-(2-methoxyethyl)polypropylene glycols such as Jeffamine™ ED-600, unhindered diamines such as Jeffamine™ EDR-148 polyetheramine. 4,7,10-trioxa-1,13-tridecanediamine. Boc-N-amido-dPEG$_{11}$-amine. Boc-N-amido-dPEG$_3$-amine, beta-alanine, aminocaproic acid, amino-PEG$_n$-carboxylate compounds (where n is between 2 and 20), succinic acid, succinic anhydride, glutaric acid, glutaric anhydride, diglycolic acid, diglycolic anhydride, thioglycolic acid, N-succinimidyl S-acetylthioacetate, N-succinimidyl S-acetylthiopropionate, N-acetyl homocysteine thiolactone. 8-mercaptooctanoic acid, alpha-lipoic acid, lipoamide-PEG$_n$-carboxylate compounds (where n is between 2 and 20), thiol-PEG$_n$-carboxylate compounds (where n is between 2 and 20). NHS-PEG$_n$-acetylated thiol compounds, dithiothreitol (DTT) (where n is between 2 and 20), tetra(ethylene glycol) dithiol, hexa (ethylene glycol) dithiol, poly(ethylene glycol) dithiol. 2-mercaptoethylamine, adipic dihydrazide and carbohydrazide.

In another aspect, the transaminase enzyme is cross-linked to another enzyme. In specific instances the transaminase enzyme is covalently cross-linked to another transaminase enzyme. In more specific examples, this cross linking is mediated by reacting the enzyme with a homobifunctional or heterobifunctional spacer arm to impart identical or different functionality. Spacer arms are well known in the art and include but not limited to ($C_2$-$C_{20}$)alkylene groups that may incorporate one or more hetero atom, aromatic groups, alkylaromatic groups, amido groups, amino groups, urea groups, carbamate groups, ether groups, thio ether groups, and the like and combinations thereof. In an embodiment, the spacer arm is one or more selected from the group consisting of ethylenediamine, 1,3-diamino-2-propanol, diaminodipropylamine (DADPA), cystamine, 1,6-diaminohexane, O-(2-Aminopropyl)-O'-(2-methoxyethyl)polypropylene glycols such as Jeffamine™ ED-600, unhindered diamines such as Jeffamine™ EDR-148 polyetheramine, 4,7,10-trioxa-1,13-tridecanediamine, Boc-N-amido-dPEG$_{11}$-amine, Boc-N-amido-dPEG$_3$-amine, beta-alanine, aminocaproic acid, amino-PEG$_n$-carboxylate compounds (where n is between 2 and 20), succinic acid, succinic anhydride, glutaric acid, glutaric anhydride, diglycolic acid, diglycolic anhydride, thioglycolic acid, N-succinimidyl S-acetylthioacetate, N-succinimidyl S-acetylthiopropionate, N-acetyl homocysteine thiolactone, 8-mercaptooctanoic acid, alpha-lipoic acid, lipoamide-PEG$_n$-carboxylate compounds (where n is between 2 and 20), thiol-PEG$_n$-carboxylate compounds (where n is between 2 and 20), NHS-PEG$_n$-acetylated thiol compounds, dithiothreitol (DTT) (where n is between 2 and 20), tetra(ethylene glycol) dithiol, hexa (ethylene glycol) dithiol, poly(ethylene glycol) dithiol, 2-mercaptoethylamine, adipic dihydrazide and carbohydrazide.

As used herein, a transamination solvent refers to an organic solvent used to assist with the reduction of a ketone to an amine catalyzed by a transaminase enzyme. In embodiments of the invention, a transamination solvent is independently selected from 2-methyl THF, THF, MTBE, CPME, toluene, ethyl acetate, IPAc, DMSO, IPA, acetonitrile, DMF, NMP or DMAc. In some embodiments the transamination solvent is independently selected from 2-methyl THF or IPAc.

A water-containing transamination solvent refers to a transamination solvent to which water was added to increase the water content of the solvent. In some embodiments the water-containing transamination solvent is independently selected from water-containing 2-methyl THF or IPAc.

As used herein, the phrase "water saturation point" refers to the point at which a given solvent is unable to absorb or dissolve more water. For example, for an organic solvent that is one homogeneous solution, if the water saturation point is surpassed, two phases, an aqueous phase and an organic phase, will be observed.

In embodiments of the invention, a continuous reaction system is used. Examples of continuous reaction systems include, but are not limited to, packed-bed reactors (PBRs), fixed bed reactors, moving bed reactors, rotating bed reactors, fluidized bed reactors, slurry reactors, batch stirred tank reactors, continuous stirred tank reactors, membrane reactors, tube-in-tube reactors, monolith reactors, microstructured reactors, fluidized bed reactors and the like.

Immobilizations may be performed using a variety of methods know to those skilled the art. These methods comprise combining a transaminase enzyme with a solid support in reactor configurations including but not limited to batch reactors or continuous reaction systems as defined above.

As used herein, a weakly coordinating solvent refers to solvents that may comprise a weakly Lewis basic heteroatom. In embodiments of the invention, the weakly coordinating solvent or mixtures thereof is independently selected from sulfolane, acetonitrile, DME, ethylene glycol or propylene carbonate. In particular embodiments, if sulfolane is used, the organic solvent is independently selected from anisole, toluene, chlorobenzene, dichloromethane or 1,2-dichloroethane.

In embodiments of the invention, sulfolane can be replaced by other sulfones, including but not limited to dialkyl sulfones, alkyl aryl sulfones or diaryl sulfones, such as isopropyl methyl sulfone, di-isopropyl sulfone, di-n-butyl sulfone, diphenyl sulfone, bis(4-methylphenyl) sulfone.

As used herein, a silane reductant refers to silane compounds that can be used as reducing agents. In embodiments of the invention, the silane reductant is selected from triethylsilane, chlorodimethylsilane, phenylsilane, ethoxy dimethylsilane, diethoxymethylsilane, triethoxysilane, and 1,1,3,3-tetramethyldisiloxane. In further embodiments, the silane reductant is selected from chlorodimethylsilane, phenylsilane, ethoxydimethylsilane, diethoxymethylsilane and 1,1,3,3-tetramethyldisiloxan. In other embodiments, the silane reductant is selected from chlorodimethylsilane, phenylsilane or triethylsilane. In particular embodiments, the silane reductant is selected from chlorodimethylsilane, or triethylsilane.

As used herein, a borane reductant refers to borane compounds that can be used as reducing agents. In embodiments of the invention, the borane reductant is selected from borane-tetrahydrofuran complex, borane-dimethylsulfide complex, borane-N,N-diethylaniline complex, sodium borohydride (NaBH4), sodium borohydride with trifluoroacetic acid, and sodium cyanoborohydride.

In embodiments of the invention, the Lewis acid is selected from boron trifluoride diethyl etherate, boron trifluoride tetrahydrofuran complex, aluminum trichloride and trimethylsilyltriflate. In further embodiments, the Lewis acid is selected from boron trifluoride diethyl etherate, or trimethylsilyltriflate.

In embodiments of the invention, the alcohol is independently selected from methanol, ethanol, or isopropanol. In further embodiments, the alcohol is methanol.

As used herein, an antisolvent refers to a solvent that reduces the solubility of the solute. In embodiments of this invention, the antisolvent is independently selected from 2-methyl THF, MTBE, CPME, THF, acetonitrile, and $C_3$-$C_{10}$ alkyl alcohols such as, but not limited to isopropanol, propanol or n-butanol.

As used herein, a sealed reactor refers to a reaction vessel in which one can conduct chemical reactions under pressure such as an autoclave reactor. A reactor capable of controlling the reaction pressure includes but is not limited to a reactor equipped with a pressure control valve, or a manual or an automatic backpressure regulator.

In embodiments of the invention, the pressure is controlled between 3.5 psig-80 psig. Those skilled in the art will recognize that the reaction pressure is depended on the vessel fill, the volume of the reactor occupied by the reaction mixture, in the reactor.

In embodiments of the invention, the organic solvent or a mixture of organic solvents is independently selected from sulfolane, acetonitrile, DME, 2-methyl THF, THF, CPME, DCM, DCE or combinations thereof. In particular embodiments, the organic solvent is DME.

In embodiments of the invention, the organic base is independently selected from tertiary amine bases such as but not limited to DIPEA, triethylamine, DABCO, DBU and DBN. In particular embodiments, the base is DIPEA.

In embodiments of the invention, the first base is selected from methyllithium in diethyl ether, methyl lithium in diethoxymethane, methyl lithium-lithium bromide complex. In particular embodiments, the first base is methyl lithium in diethoxymethane.

In embodiments of the invention, the second base is selected from n-butyllithium in hexanes, n-butyllithium in heptane, n-butyllithium in toluene, n-butyllithium in cyclohexanes, n-hexyllithium in hexanes. In further embodiments, the second base is selected from n-butyllithium in hexanes and n-hexyllithium in hexanes.

As used herein, an aprotic solvent refers to organic solvents that lack the presence of acidic protons. In embodiments of this invention, the first and second aprotic solvents are independently selected from THF, 2-methyl THF, MTBE, diethyl ether, CPMe, DCM or DCE. In particular embodiments, the first and second aprotic solvents are THF.

In embodiments of the invention, the aqueous solution is independently selected from water, aqueous hydrochloric acid, aqueous hydrobromic acid, aqueous acetic acid, aqueous ammonium chloride, aqueous sodium chloride, or a mixture of aqueous sodium chloride containing acetic acid. In further embodiments, the aqueous solution is selected from aqueous acetic acid, aqueous sodium chloride containing acetic acid or aqueous ammonium chloride.

As used herein, a reaction solvent refers to an organic solvent used to assist in the reaction of preparing Compound A. In embodiments of the invention, the reaction solvent is independently selected from an alcohol, 2-methyl THF, THF, MTBE, CPME, acetonitrile, dichloromethane, 1,2-dichloroethane, DMF, NMP or DMAc. In some embodiments the reaction solvent is an alcohol, which is independently selected from methanol, ethanol, isopropanol, or tert-amyl alcohol. In further embodiments, the reaction solvent is ethanol.

As used herein, a crystallization solvent refers to a solvent that reduces the solubility of the solute Compound A. In embodiments of the invention, the crystallization solvent is independently selected from water, toluene, anisole, 2-methyl THF, THF, MTBE, CPME, DCM, hexanes, heptane or an alcohol. In some embodiments, the crystallization solvent is water.

In the first embodiment of the invention, the co-factor is PLP, the buffer solution is aqueous sodium tetraborate and the transaminase enzyme is selected from Enzyme 1 (SEQ ID NO: 1) or Enzyme 6 (SEQ ID NO: 6).

In the second embodiment of the invention, the inorganic base is selected from sodium hydroxide or potassium hydroxide, the solvent is independently selected from 2-methyl THF or IPAc, the inorganic salt is potassium carbonate or potassium phosphate, and the acid is p-toluenesulfonic acid or hydrochloric acid.

In the third embodiment of the invention, the inorganic base is selected from sodium hydroxide or potassium hydroxide, the base is sodium hydroxide, the solvent is independently selected from 2-methyl THF and MTBE, and the acid is p-toluenesulfonic acid or hydrochloric acid.

In the fourth embodiment of the invention, the transaminase enzyme is selected from Enzyme 1 or Enzyme 6, the buffer solution is aqueous potassium phosphate, the solid support is a polymeric resin selected from Diaion® Hp2mgL, Diaion® SP2mgL, Purolite® ECR8415F, Purolite® ECR8415M, the transamination solvent is independently selected from water-containing 2-methyl-THF or IPAc, and the acid is p-toluenesulfonic acid or hydrochloric acid.

In the fifth embodiment of the invention, the weakly coordinating solvent is a mixture of anisole and sulfolane, the silane reductant is selected from triethylsilane or phenylsilane, the Lewis acid is boron trifluoride diethyl etherate and the alcohol is methanol.

In the fifth embodiment, after adding the alcohol in step c), a pharmaceutically acceptable acid may be added to obtain the desired pharmaceutically acceptable salt of Compound 4.

In the sixth embodiment of the invention, the weakly coordinating solvent is a mixture of anisole and sulfolane, the silane reductant is selected from triethylsilane or phenylsilane Lewis acid is boron trifluoride diethyl etherate and the alcohol is methanol.

In the seventh embodiment of the invention, the organic solvent is DME, the organic base is DIPEA, and the silane reductant is chlorodimethylsilane.

In the eighth embodiment of the invention, the first base is methyl lithium in diethoxymethane, the aprotic solvent is THF, the second base is selected from n-butyllithium in hexanes or n-hexyllithium in hexanes, the aqueous solution is selected from aqueous acetic acid, aqueous sodium chloride containing acetic acid or aqueous ammonium chloride, and the alcohol is ethanol.

In the ninth embodiment of the invention, the base is DIPEA, the reaction solvent is ethanol, and the crystallization solvent is water.

In some occurrences, the transaminase enzyme is based on the amino acid sequences of SEQ ID NO: 1, 2, 3, 4, 5, 6, 7, 8, and the like, and can comprise an amino acid sequence that is at least about 85%, 86%, 87%, 88%, 89%, 90%, 91%, 92%, 93%, 94%, 95%, 96%, 97%, 98%, or 99% identical to the reference sequence of SEQ ID NO: 1, 2, 3, 4, 5, 6, 7 or 8. These differences can be amino acid insertions, deletions, substitutions, or any combinations of such changes. In some occurrences, the amino acid sequence differences can comprise non-conservative, conservative, as well as a combination of non-conservative and conservative amino acid substitutions.

In some embodiments, such transaminase polypeptides are also capable of converting the substrate to the product with a diastereomeric ratio of at least 15:1. In some embodiments, such transaminase polypeptides are also capable of converting the substrate to the product with a diastereomeric ratio of at least 25:1. In some embodiments, such transaminase polypeptides are also capable of converting the substrate to the product with a diastereomeric ratio of at least 70:1.

In some embodiments, the transaminase polypeptide is highly stereoselective, wherein the polypeptide can reduce the substrate to the product in greater than about 50:1, 60:1 and 70:1 diastereomeric ratio.

"Amino acids" are referred to herein by either their commonly known three-letter symbols or by the one-letter symbols recommended by IUPAC-IUB Biochemical Nomenclature Commission. Nucleotides, likewise, may be referred to by their commonly accepted single letter codes.

The abbreviations used for the genetically encoded amino acids are conventional and are as follows: alanine (Ala or A), arginine (Arg or R), asparagine (Asn or N), aspartate (Asp or D), cysteine (Cys or C), glutamate (Glu or E), glutamine (Gln or Q), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

"Protein," "polypeptide," and "peptide" are used interchangeably herein to denote a polymer of at least two amino acids covalently linked by an amide bond, regardless of length or post-translational modification (e.g., glycosylation, lipidation, myristylation, phosphorylation, ubiquitination, etc.). Included within this definition are D- and L-amino acids, and mixtures of D- and L-amino acids, as well as polymers comprising D- and L-amino acids, and mixtures of D- and L-amino acids.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage (%) sequence identity," "percent identity," and "percent identical" are used herein to refer to comparisons between polynucleotide sequences or polypeptide sequences, and are determined by comparing two optimally aligned sequences over a comparison window; wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410; and Altschul et al., 1977, Nucleic Acids Res. 3389-3402). Software for performing BLAST analyses is publicly available through the National Center for Biotechnology Information website.

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, n USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison WI), using default parameters provided.

"Substantial identity" refers to a polynucleotide or polypeptide sequence that has at least 80 percent sequence identity, preferably at least 85 percent sequence identity, more preferably at least 89 percent sequence identity, more preferably at least 95 percent sequence identity, and even more preferably at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, more preferably at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (EE) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (DE). Enantiomeric excess and diastereomeric excess are types of stereomeric excess.

"Highly stereoselective" refers to a chemical or enzymatic reaction that is capable of converting a substrate to its corresponding product with at least about 85% stereoisomeric excess.

"Conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a polypeptide can be expressed as "percent conversion" of the substrate to the product.

Immobilized enzyme preparations have a number of recognized advantages. They can confer shelf stability to enzyme preparations, they can improve enzyme stability in organic solvents, and they can aid in protein removal from reaction streams, as examples. "Stable" refers to the ability of the immobilized enzymes to retain their structural conformation and/or their activity under given conditions, for instance in a solvent system that contains organic solvents. Stable immobilized enzymes lose less than 10% activity per hour in a solvent system that contains organic solvents. Stable immobilized enzymes lose less than 9% activity per hour in a solvent system that contains organic solvents. Preferably, the stable immobilized enzymes lose less than 8% activity per hour in a solvent system that contains organic solvents. Preferably, the stable immobilized enzymes lose less than 7% activity per hour in a solvent system that contains organic solvents. Preferably, the stable immobilized enzymes lose less than 6% activity per hour in a solvent system that contains organic solvents. Preferably, the stable immobilized enzymes lose less than 5% activity per hour in a solvent system that contains organic solvents. Preferably, the stable immobilized enzymes less than 4% activity per hour in a solvent system that contains organic solvents. Preferably, the stable immobilized enzymes lose less than 3% activity per hour in a solvent system that contains organic solvents. Preferably, the stable immobilized enzymes lose less than 2% activity per hour in a solvent system that contains organic solvents. Preferably, the stable immobilized enzymes lose less than 1% activity per hour in a solvent system that contains organic solvents.

As used herein, "polynucleotide" and "nucleic acid" refer to two or more nucleotides that are covalently linked together. The polynucleotide may be wholly comprised of ribonucleotides (i.e., RNA), wholly comprised of 2' deoxyribonucleotides (i.e., DNA), or comprised of mixtures of ribo- and 2' deoxyribonucleotides, and may include a DNA or RNA of genomic, mRNA, cDNA, or synthetic origin, or some combination thereof. While the nucleosides will typically be linked together via standard phosphodiester linkages, the polynucleotides may include one or more nonstandard linkages. The polynucleotide may be single-stranded or double-stranded, or the polynucleotide may include both single-stranded regions and double-stranded regions. Moreover, while a polynucleotide will typically be composed of the naturally occurring encoding nucleobases (i.e., adenine, guanine, uracil, thymine and cytosine), it may include one or more modified and/or synthetic nucleobases, such as, for example, inosine, xanthine, hypoxanthine, etc. In some embodiments, such modified or synthetic nucleobases are nucleobases encoding amino acid sequences.

As used herein, the terms "biocatalysis," "biocatalytic," "biotransformation," and "biosynthesis" refer to the use of enzymes to perform chemical reactions on organic compounds.

As used herein, "deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an evolved enzyme. Deletions can be directed to the internal portions and/or terminal portions of the polypeptide. In various embodiments, the deletion can comprise a continuous segment or can be discontinuous. Deletions are typically indicated by "-" in amino acid sequences.

As used herein, "insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

The term "amino acid substitution set" or "substitution set" refers to a group of amino acid substitutions in a polypeptide sequence, as compared to a reference sequence. A substitution set can have 1, 2, 3, 4, 5, 6, 7, 8, 9, 10, 11, 12, 13, 14, 15, or more amino acid substitutions.

As used herein, "isolated polypeptide" refers to a polypeptide that is substantially separated from other contaminants that naturally accompany it (e.g., protein, lipids, and polynucleotides). The term embraces polypeptides that have been removed or purified from their naturally occurring environment or expression system (e.g., within a host cell or via in vitro synthesis). The recombinant polypeptides may be present within a cell, present in the cellular medium, or prepared in various forms, such as lysates or isolated preparations. As such, in some embodiments, the recombinant polypeptides can be an isolated polypeptide.

Exemplary methods and materials are described herein, although methods and materials similar or equivalent to those described herein can also be used in the practice or testing of the present disclosure. The materials, methods, and examples are illustrative only and not intended to be limiting. The transaminase enzymes were used as lyophilized cell-free lysate powders. Unless otherwise indicated, solvents and reagents were commercially available and were used as received.

Scheme

The overall process of the present invention to synthesize (2-Chloro-4-phenoxyphenyl)(4-{[(3R,6S)-6-(hydroxymethyl)oxan-3-yl]amino}-7H-pyrrolo[2,3-d]pyrimidin-5-yl) methanone or Compound A is summarized in the following Scheme 1. The overall process is a highly convergent synthesis wherein Compound A is prepared from a reaction between two intermediates; (2-Chloro-4-phenoxyphenyl)(4-chloro-7H-pyrrolo[2,3-d]pyrimidin-5-yl)methanone, herein referred to as Compound 7; and an appropriate salt of (3R,6S)-6-(Hydroxymethyl)oxan-3-amine, herein referred to as Compound 4'.

Scheme 1.

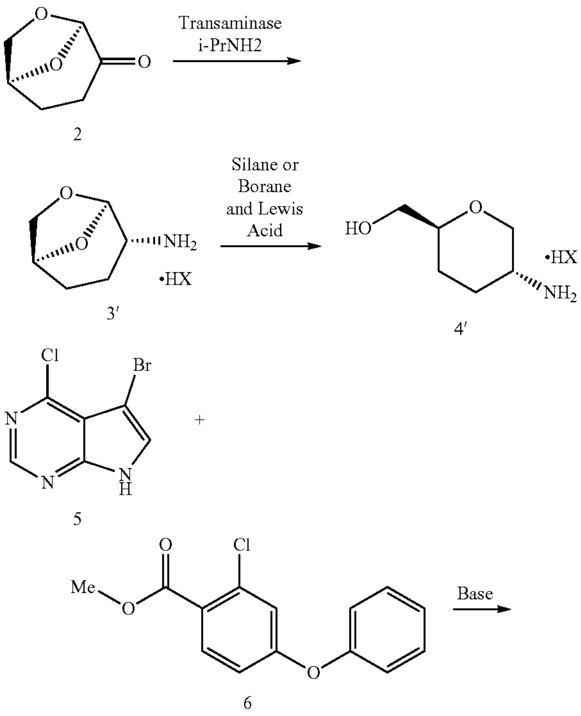

-continued

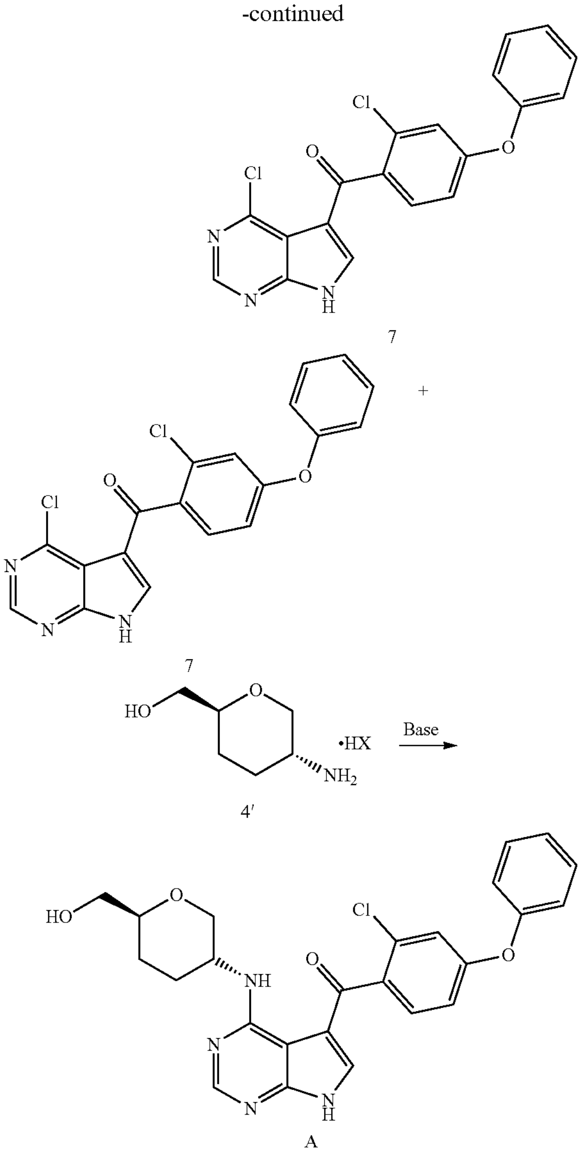

wherein X is TsO or Cl

This present invention describes a protecting group-free synthetic route to an appropriate salt of Compound 4' starting from (1S,5R)-6,8-Dioxabicyclo[3.2.1]octan-4-one, herein referred to as Cyrene or Compound 2, a bio-renewable material readily obtained through pyrolysis of biomass.

It has been found that recombinant transaminase enzymes are capable of catalyzing the conversion of Compound 2 to (1S,4R,5R)-6,8-Dioxabicyclo[3.2.1]octan-4-amine, herein referred to as Compound 3, in good diastereoselectivity when isopropylamine is used as an amino group donor.

As described herein, these transamination reactions can be performed in aqueous solutions followed by a suitable work-up method to isolate water-soluble Compound 3 as a salt. Performing transamination reactions in aqueous solutions by applying vacuum or a nitrogen sweep to remove the acetone by-product can improve the yield and purity of Compound 3 since an aldol side-reaction between Cyrene (2) and the acetone by-product is minimized through acetone removal.

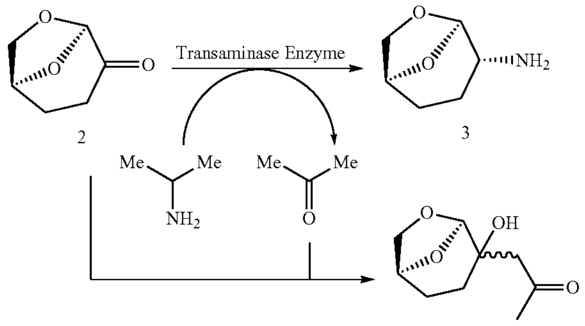

2

3 aldol side-reaction product

Alternatively, the present invention describes the process for preparing Compound 3 using immobilized transaminase enzymes in an organic solvent. This approach greatly simplifies protein removal from, and isolation of the water-soluble Compound 3. Instead of tedious extraction and enzyme denaturation procedures, Compound 3 can be directly isolated from the organic solvent as a salt.

The transamination reaction using immobilized transaminase enzymes may be performed in batch, wherein the immobilized transaminase enzyme can be filtered away after the reaction is complete. The reaction using immobilized transaminase enzymes may also be performed in a rotating bed or spinning basket reactor, wherein the immobilized transaminase enzyme is retained in the basket and product can be collected without filtration. Alternatively, the transamination reaction may be performed in a continuous reaction system wherein the reaction stream is continuously passed over the immobilized transaminase enzyme and the product is collected. The latter approach further streamlines handling of the immobilized transaminase enzyme and improves the efficiency of the transamination reaction by increasing the amount of product obtainable per kg of enzyme.

The transamination reactions described herein produce Compound 3 as the major product and (1S,4S,5R)-6,8-Dioxabicyclo[3.2.1]octan-4-amine (3d), the cis-diastereomer of Compound 3, as the minor product.

3d

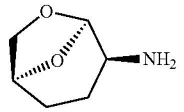

Those skilled in the art will recognize that the diastereometric ratio of Compound 3 and 3d depends on the choice of transaminase enzyme, the choice of transamination solvent, the reaction temperature and the reaction time. The diastereomeric ratio of Compound 3 and 3d for a given enzyme also depends on whether the transaminase enzyme is used in an aqueous solvent or whether it is immobilized on a solid support. For transamination reactions described herein, the diastereomeric ratio decreases upon immobilization of a given transaminase enzyme on a solid support. This effect is demonstrated by, but not limited to, Example 1A vs. Example 1C. Further upgrade of the diastereomeric ratio is obtained during the isolation of Compound 3 as a salt 3'. The addition of water during the isolation of compound 3 as a salt 3' can further improve the diastereomeric ratio.

In a further aspect, the present invention describes the conversion of Compound 3 or salts thereof to Compound 4'. This previously unprecedented transformation was found to proceed by combining Compound 3' with a borane or silane reductant and a Lewis acid. In particular, the present invention describes the process for preparing Compound 4' using triethyl silane and boron trifluoride diethyl etherate in the presence of sulfolane as an organic solvent. This reagent and solvent combination were found to generate diborane, the active reductant, and triethylsilylfluoride in situ. Due to the gaseous nature of the active reductant, it is beneficial to allow pressure build up during the formation of 4' by performing the reaction in a sealed reactor or reactor vessels capable of controlling the reaction pressure.

Additionally, a process for preparing Compound 7 from commercially available 5-Bromo-4-chloro-7H-pyrrolo[2,3-d]pyrimidine, herein referred to as Compound 5, and Methyl 2-chloro-4-phenoxy benzoate, herein referred to as Compound 6 is also described. The process for preparing Compound 7 may be performed in batch as commonly known by anyone skilled in the art. As presented herein, the process for preparing Compound 7 may be performed in a continuous reaction system to avoid the need of cryogenic temperatures.

ABBREVIATIONS

Measurements g/L grams per liter
mg milligram
min minutes
ml, mL milliliter
mM millimolar, 1 mM is a concentration of one thousandth of a mole per liter
mmol millimole, a thousandth of a mole (the amount of any chemical substance that equals the number of atoms in 12 grams of carbon-12).
N Normality, the gram equivalent weight of a solution in a solution, which is its molar concentration divided by an equivalence factor.
rpm Revolutions per minute
ul, uL, µl, µL microliter
CPME cyclopentyl methyl ether
DABCO 1,4-diazabicyclo[2.2.2]octane
DBN 1,5-Diazabicyclo[4.3.0]non-5-ene
DBU 1,8-Diazabicyclo[5.4.0]undec-7-ene
DIPEA N,N-diisopropylethyl amine
DCM dichloromethane
DCE 1,2-dichloroethane
DMAc N,N-dimethylacetamide
DME 1,2-dimethoxyethane
DMF N,N-dimethylformamide
$iPrNH_2$ Isopropylamine
LB broth Luria-Bertani Broth, commercially available, nutritionally rich medium for culture and growth of bacteria
NMP N-methyl 2-pyrrolidone
Boc tert-butoxy carbonyl
IPA isopropanol
IPAc isopropyl acetate
KOH potassium hydroxide
2-methylTHF 2-methyltetrahydrofuran
MTBE methyl tert-butyl ether
NaOH sodium hydroxide
OD600 Optical Density at 600 nm packed-bed reactor PBR
pCK110900 Expression System of Recombinant Proteins in *E. coli*
polyethylene glycol PEG
Ph Phenyl
pyridoxal 5'-phosphate PLP
PMP pyridoxamine 5'-phosphate
TB Terrific Broth, commercially available, nutritionally rich medium for culture and growth of bacteria
THF tetrahydrofuran
TMS trimethylsilyl
TsOH p-toluenesulfonic acid Additional abbreviations may be defined throughout this disclosure.

EXAMPLES

Example 1A: Preparation of (1S,4R,5R)-6,8-Dioxabicyclo[3.2.1]octan-4-aminium 4-methylbenzene-1-sulfonate (3a)

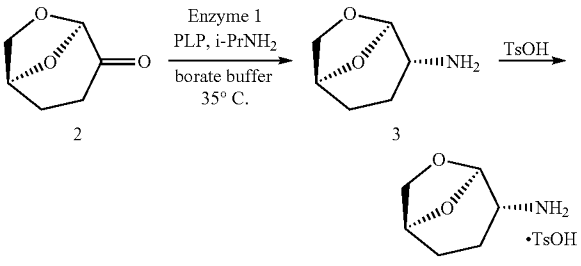

2 3 3a

Pyridoxal 5'-phosphate monohydrate (1 g) was dissolved in 500 mL buffer (0.1 M sodium tetraborate with 1.56 M isopropylamine at pH 9.5). Enzyme 1 (SEQ ID NO: 1) (10 g, 20 wt %) was then added and dissolved at room temperature. (Enzyme 1 is commercially available as lyophilized cell-free lysate from Codexis, Inc., Redwood City, California). (1S,5R)-6,8-Dioxabicyclo[3.2.1]octan-4-one (2) (49.9 g, 389 mmol) was then added, and the mixture was heated to 33-37° C. for 27 h. During the reaction, vacuum and nitrogen flow were applied to remove the acetone generated. The pH was adjusted over the course of the reaction to keep the pH between 7.9 and 8.6 yielding a solution of (1S,4R,5R)-6,8-Dioxabicyclo[3.2.1]octan-4-amine (3) (15:1 d.r.).

The reaction described was adjusted to pH 13.4 with 50 wt % NaOH solution (28 mL). The mixture was cooled to 10-15° C., and potassium carbonate (83.3 g) was added slowly maintaining the temperature below 25° C. 2-Methyl THF (300 mL) was added, and the resulting mixture was stirred at room temperature overnight to allow for enzyme denaturing. The denatured protein solids were then filtered off and the filter cake was washed with 2-methyl THF (3×50 mL). The aqueous filtrate was extracted with 2-MeTHF (75 mL). The combined organic layers were concentrated under reduced pressure to remove isopropylamine. 2-Methyl THF was then added to the resulting solution of (1S,4R,5R)-6,8-Dioxabicyclo[3.2.1]octan-4-amine (3) to adjust total volume to 200 mL. Water was then added to adjust the water content to 3-3.6 wt %. p-toluenesulfonic acid monohydrate (73.6 g, 387 mmol) in 2-methyl THF (150 mL) was then added dropwise over 4 h at 40° C. The resulting slurry was cooled to room temperature and aged for 2 h. The batch was filtered. The filter cake was washed with wet (2 wt % water) 2-methyl THF (50 mL) and dry 2-methylTHF (50 mL). The wet cake was dried at 50° C. overnight, to yield 3a as a solid (92.1 g, 79% yield, 127:1 dr). mp 227° C. (DSC); $^1$H NMR (DMSO-$d_6$, 500 MHz) δ 7.96 (br s, 3H), 7.49 (d, 2H, J=8.0 Hz), 7.13 (d, 2H, J=8.0 Hz), 5.40 (s, 1H), 4.61 (s, 1H), 3.98 (d, 1H, J=7.3 Hz), 3.68 (m 1H), 3.12 (br m, 1H), 2.30 (s, 3H), 2.04 (m, 2H), 1.57 (m, 1H), 1.43 (m, 1H) ppm; $^{13}$C NMR (DMSO-$d_6$, 125 MHz) δ 145.6, 138.5, 128.7, 125.9, 99.1, 73.5, 67.5, 47.9, 23.7, 21.3, 19.1 ppm.

Example 1B: Preparation of (1S,4R,5R)-6,8-Dioxabicyclo[3.2.1]octan-4-aminium 4-methylbenzene-1-sulfonate (3a)

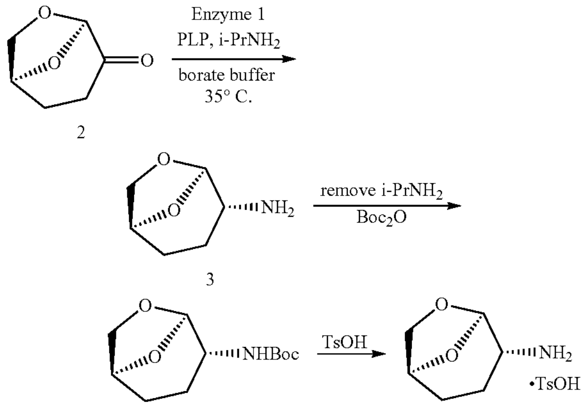

2 3 3c 3a

Pyridoxal 5'-phosphate monohydrate (500 mg) was dissolved in 250 mL buffer (0.1 M sodium tetraborate with 1.56 M isopropylamine at pH 9.8). Enzyme 1 (SEQ ID NO: 1) (3.75 g, 15 wt %) was then added and dissolved at room temperature. (1S,5R)-6,8-Dioxabicyclo[3.2.1]octan-4-one (2) (25 g, 195 mmol) was then added, and the mixture was heated to 35° C. for 29 h. During the reaction, vacuum and air flow were applied to remove the acetone generated. The stream was then cooled to room temperature, and 10 mL 50 wt % NaOH were added to adjust the pH to 12. The reaction mixture was then concentrated under vacuum using a nitrogen sweep to remove isopropylamine while the pH was maintained at 12 using 50 wt % NaOH. To the reaction mixture at pH 12, a solution of di-tert-butyl dicarbonate (42.6 g, 195 mmol) in THF (62 mL) was added via syringe pump over 2.5 h at 25° C. During the addition the pH was monitored and additional 50 wt % NaOH was added to maintain the pH above 10. The reaction was aged overnight at 22-25° C. MTBE (250 mL) was then charged and the mixture was stirred for 2 h. The batch was filtered, and the solids were washed with MTBE. The layers of the filtrate were separated, and the aqueous layer was extracted with MTBE (150 mL). The combined organic layers were washed with 15 wt % NaCl (100 mL) and concentrated. 2-MeTHF was added, and the solution was filtered to remove solids yielding a 2-MeTHF solution of compound 3c (82.7 g). Then, 2-methyl THF (320 mL) followed by p-toluenesulfonic acid monohydrate (100 g, 581 mmol) were charged and the reaction was heated to 35° C. and aged overnight. The resulting slurry was then cooled to 21° C. and aged for 4 h. The slurry was filtered, washed with 2-MeTHF (2×100 mL) and dried under vacuum yielding 3a as a solid (43.5 g, 74.0% yield, >30:1 d.r.). mp 227° C. (DSC); $^{1}$H NMR (DMSO-$d_6$, 500 MHz) δ 7.96 (br s, 3H), 7.49 (d, 2H, J=8.0 Hz), 7.13 (d, 2H, J=8.0 Hz), 5.40 (s, 1H), 4.61 (s, 1H), 3.98 (d, 1H, J=7.3 Hz), 3.68 (m 1H), 3.12 (br m, 1H), 2.30 (s, 3H), 2.04 (m, 2H), 1.57 (m, 1H), 1.43 (m, 1H) ppm; $^{13}$C NMR (DMSO-$d_6$, 125 MHz) δ 145.6, 138.5, 128.7, 125.9, 99.1, 73.5, 67.5, 47.9, 23.7, 21.3, 19.1 ppm.

As used herein, d.r. is used to denote "diastereomeric ratio". The first digit denotes the fraction of the product that is the (1S,4R,5R)-6,8-dioxabicyclo[3.2.1]octan-4-amine, while the second digit denotes the fraction of the product that is (1S,4S,5R)-6,8-dioxabicyclo[3.2.1]octan-4-amine.

Example 1C: Preparation of (1S,4R,5R)-6,8-Dioxabicyclo[3.2.1]octan-4-aminium 4-methylbenzene-1-sulfonate (3a)

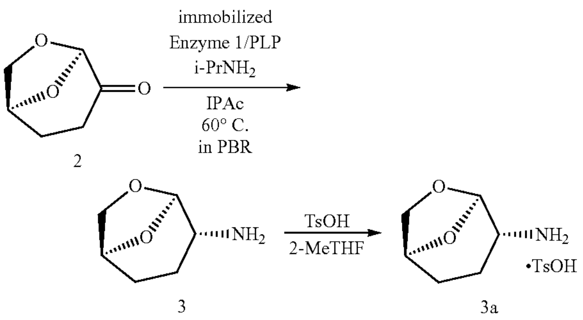

Pyridoxal 5'-phosphate monohydrate (13.7 g) was added to a 100 mM potassium phosphate buffer pH 7.0 (1.67 L) and the mixture was cooled to 4° C. The pH was adjusted using 1 N KOH (58 g) to pH 6.95. Enzyme 1 (334.6 g) was then charged over 1.25 h. The resin Diaion® HP2MGL (2.50 kg, hydrated) was then added, and the mixture was incubated at 4° C. for 60 h. The mixture was then diluted with 1.75 L water and agitated for 15 min. The immobilized transaminase slurry was packed into a 1.7 L jacketed column cooled to 5° C. The column was washed with water at a linear velocity of 2.5 cm/min for 140 min, and then washed with an isopropanol:PEG-400:water mixture (88:10:2 wt %) at a linear velocity of 1.5-2.5 cm/min for 150 min. The column was warmed to 20° C., and the isopropanol:PEG-400:water mixture was flowed through the column until the effluent reached 18° C. Water-saturated isopropyl acetate was then flowed through the column at a linear velocity of 2.5 cm/min for 135 min. The column was heated to 60° C. The reaction stream was prepared by combining (1S,5R)-6,8-Dioxabicyclo[3.2.1]octan-4-one (2) (2.0 kg, 15.6 mol), isopropylamine (1.153 kg. 19.5 mol, 1.25 equivalents), and 16.8 L water-saturated isopropyl acetate at room temperature. The mixture was flowed through the column with a residence time of 3 h. The stream was diverted for the first 15 h (5 column volumes), and then the product stream was collected for 72 h, providing a solution of (1S,4R,5R)-6,8-Dioxabicyclo[3.2.1]octan-4-amine (3) (13.7 kg, 8.06 wt. % 3, 13:1 d.r.).

The mixture was then concentrated under reduced pressure to approximately 3 L (~3 volumes relative to starting material) and then flushed with 5.5 L isopropyl acetate to a final volume of 3 L. The solution was then warmed to 35° C. and a solution of p-toluenesulfonic acid monohydrate (1.65 kg, 8.67 mol) in 2-methyl THF (6.5 L) was added over the course of 1.5 h. The resulting slurry was aged at 37-40° C. for 30 min and then stirred at room temperature overnight. The slurry was filtered, and the wet cake was washed with 2-methyl THF (2×6 L). The cake was dried under vacuum/$N_2$ sweep for 18 h to provide 3a as a solid (2.4 kg, 71% yield 2.4 kg. 71% yield based on amount of Compound 2 flowed during 72 h, 35:1 dr). mp 227° C. (DSC); $^{1}$H NMR (DMSO-$d_6$, 500 MHz) δ 7.96 (br s, 3H), 7.49 (d, 2H, J=8.0 Hz), 7.13 (d. 2H, J=8.0 Hz), 5.40 (s, 1H), 4.61 (s, 1H), 3.98 (d, 1H, J=7.3 Hz), 3.68 (m 1H), 3.12 (br m, 1H), 2.30 (s, 3H), 2.04 (m, 2H), 1.57 (m, 1H), 1.43 (m, 1H) ppm; $^{13}$C NMR (DMSO-$d_6$, 125 MHz) δ 145.6, 138.5, 128.7, 125.9, 99.1, 73.5, 67.5, 47.9, 23.7, 21.3, 19.1 ppm.

Example 1D: Preparation of (1S,4R,5R)-6,8-Dioxabicyclo[3.2.1]octan-4-aminium 4-methylbenzene-1-sulfonate (3a)

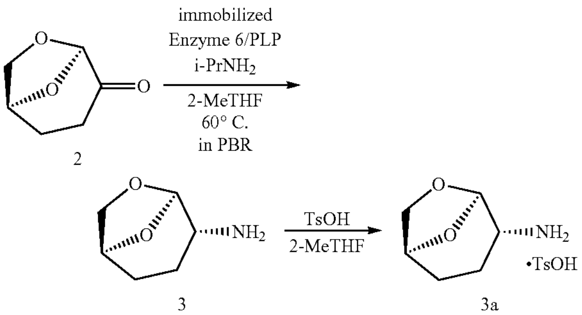

Pyridoxal 5'-phosphate monohydrate (0.716 g) was added to a 100 mM potassium phosphate buffer pH 7.0 (102 mL) and the mixture was cooled to 4° C. The pH was adjusted using 1 N KOH (4.63 g) to pH 6.80. Enzyme 6 (SEQ ID NO: 6) (17.9 g) was then charged in 4 shots and the resulting mixture was aged for 1 h. The resin Diaion® HP2MGL (150 g, hydrated) was then added, and the mixture was incubated at 4° C. for 60 h.

The immobilized transaminase slurry was then packed into a 10 mm×300 mm glass jacketed column cooled to 4° C. The column was washed with 118 mL of water at a linear velocity of 2 cm/min, and then washed with 175 mL of isopropanol:PEG-400:water mixture (86:10:4 wt %) at a linear velocity of 2 cm/min. The column was warmed to 20° C., and 118 mL of water-saturated 2-MeTHF was then flowed through the column at a linear velocity of 2 cm/min. The column was heated to 60° C. The reaction stream was prepared by combining (1S,5R)-6,8-Dioxabicyclo[3.2.1]octan-4-one (2) (100 g, 0.78 mol), isopropylamine (28.8 g, 0.48 mol, 1.25 equivalents), and 840 mL water-saturated 2-MeTHF at room temperature. The mixture was flowed through the column with a 90-minute residence time. The stream was collected for 71 h providing a solution of (1S,4R,5R)-6,8-Dioxabicyclo[3.2.1]octan-4-amine (3) (296.3 g, 12.6 wt % 3, 34:1 d.r.).

The mixture was then concentrated under reduced pressure to approximately 190 mL (~5 volumes relative to starting material) and then flushed with 260 mL 2-MeTHF to a final volume of 190 mL. 2.85 mL of water (1.5%) followed by 75 mL of 2-MeTHF were then added. The wet solution was then warmed to 35° C. and a solution of p-toluenesulfonic acid monohydrate (65.9 g, 347 mmol) in wet 2-MeTHF (190 mL) was over the course of 1.5 h. The resulting slurry was aged at 37-40° C. for 30 min and then stirred at room temperature overnight. The slurry was filtered, and the wet cake was washed with 2-MeTHF. The cake was dried under vacuum/$N_2$ sweep for 18 h to provide 3a as a solid (79.1 g, 76% yield, based on amount of Compound 2 flowed during 71 h, 385:1 dr). mp 227° C. (DSC); $^1H$ NMR (DMSO-$d_6$, 500 MHz) δ 7.96 (br s, 3H), 7.49 (d, 2H, J=8.0 Hz), 7.13 (d, 2H, J=8.0 Hz), 5.40 (s, 1H), 4.61 (s, 1H), 3.98 (d, 1H, J=7.3 Hz), 3.68 (m 1H), 3.12 (br m, 1H), 2.30 (s, 3H), 2.04 (m, 2H), 1.57 (m, 1H), 1.43 (m, 1H) ppm; $^{13}C$ NMR (DMSO-$d_6$, 125 MHz) δ 145.6, 138.5, 128.7, 125.9, 99.1, 73.5, 67.5, 47.9, 23.7, 21.3, 19.1 ppm.

Example 1E: Preparation of (1S,4R,5R)-6,8-Dioxabicyclo[3.2.1]octan-4-aminium 4-methylbenzene-1-sulfonate (3a)

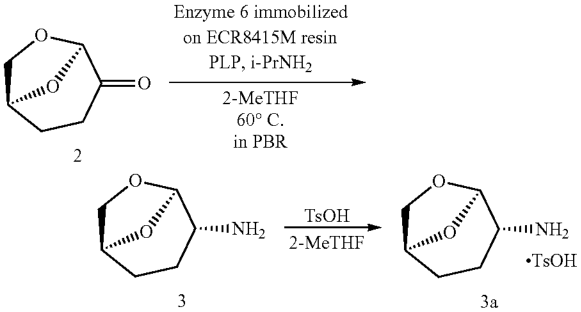

2

3

3a

Pyridoxal 5'-phosphate monohydrate (0.18 g) was added to a 100 mM potassium phosphate buffer pH 6.7 (27.3 mL) and the mixture was cooled to 4° C. Enzyme 6 (SEQ ID NO: 6) (4.50 g) was then charged and the resulting mixture was aged for 1 h. The resin ECR8415M (37.8 g, hydrated) was then added, and the mixture was incubated at 4° C. for 60 h.

The immobilized transaminase slurry was packed into a 10 mmx300 mm glass jacketed column cooled to 4° C. The column was washed with 118 mL of water at a linear velocity of 2 cm/min, and then washed with 170 mL of isopropanol:PEG-400:water mixture (86:10:4 wt %) at a linear velocity of 2 cm/min. The column was warmed to 20° C., and 118 mL of water-saturated 2-MeTHF was then flowed through the column at a linear velocity of 2 cm/min. The column was heated to 60° C. The reaction stream was prepared by combining (1S,5R)-6,8-Dioxabicyclo[3.2.1]octan-4-one (2) (200. g, 1.56 mol), isopropylamine (115 g, 1.95 mol), and 1.68 L water-saturated 2-MeTHF at room temperature. The mixture was flowed through the column with a residence time of 45 min. The stream was collected for 95 h providing a solution of (1S,4R,5R)-6,8-Dioxabicyclo[3.2.1]octan-4-amine (3) (1005 g, 10.2 wt % 3, 30:1 d.r.).

The solution (108 g) was then concentrated under reduced pressure to approximately 55 mL (~5 volumes relative to starting material) and then flushed with 77 mL 2-MeTHF to a final volume of 55 mL. 0.82 mL of water (1.5%) followed by 22 mL of 2-MeTHF were then added. The wet solution was then warmed to 35° C. and a solution of p-toluenesulfonic acid monohydrate (19.44 g, 102 mmol) in a mixture of 2-MeTHF (55 mL) and water (1.65 mL) was added over the course of 1.5 h. The resulting slurry was aged at 37-40° C. for 30 min and then stirred at room temperature overnight. The slurry was filtered, and the wet cake was washed with 2-MeTHF. The cake was dried under vacuum/$N_2$ sweep for 18 h to provide 3a as a solid (23.0 g, 77% yield based on amount of 2 flowed during 95 h, 94:1 dr). mp 227° C. (DSC); $^1H$ NMR (DMSO-$d_6$, 500 MHz) δ 7.96 (br s, 3H), 7.49 (d, 2H, J=8.0 Hz), 7.13 (d, 2H, J=8.0 Hz), 5.40 (s, 1H), 4.61 (s, 1H), 3.98 (d, 1H, J=7.3 Hz), 3.68 (m 1H), 3.12 (br m, 1H), 2.30 (s, 3H), 2.04 (m, 2H), 1.57 (m, 1H), 1.43 (m, 1H) ppm; $^{13}C$ NMR (DMSO-$d_6$, 125 MHz) δ 145.6, 138.5, 128.7, 125.9, 99.1, 73.5, 67.5, 47.9, 23.7, 21.3, 19.1 ppm.

Example 1F: Preparation of (1S,4R,5R)-6,8-Dioxabicyclo[3.2.1]octan-4-hydrochloride (3b)

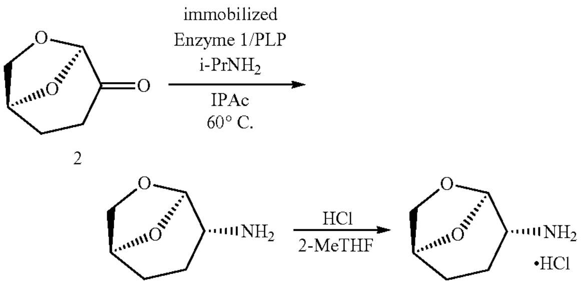

2

3

3b

Pyridoxal 5'-phosphate monohydrate (0.96 g, 3.62 mmol) was added to a 100 mM potassium phosphate buffer pH 6.9 (130.4 mL) and the mixture was aged at 4° C. for 0.25 h. Subsequently the solution pH was re-adjusted to 6.9 by addition of IN KOH (6.58 mL). Enzyme 1 (24.19 g) was then charged into the same vessel over approximately 0.5 hr followed by a rinse with additional 100 mM potassium phosphate buffer pH 6.9 (5.98 mL) and the mixture was agitated for 2 h. The resin Diaion® HP2MGL (171.77 g, hydrated) was then added, followed by a rinse with 100 mM potassium phosphate buffer pH 6.9 (11.97 mL), and the mixture was aged for 48 hr at 4° C. The resulting immobilized transaminase slurry mixture was diluted with chilled (4-8° C.) water (150 mL), agitated for 15 minutes at 4° C., and a portion transferred to a fritted filter funnel. Subsequently, the mother liquor was removed by filtering over vacuum to afford a wet cake of immobilized enzyme resin (approximately 30 g). The wet cake was then slurry washed as follows: chilled water was charged to the filter and agitated for approximately 3 minutes, subsequently the mother liquor was removed by filtration. This process was repeated three times, the first wash utilized 120 mL water, subsequent water washes used 90 mL water. Next the immobilized transaminase was similarly slurry washed, three times, with 90 mL of a chilled isopropanol:PEG-400: water mixture (88:10:2 wt %). This was followed by three similar slurry washes with 90 mL water saturated IPAc. Subsequently the excess water saturated IPAC was removed by gentle filtration yielding a wet cake of immobilized transaminase resin, a portion of which was utilized for the subsequent reaction.

Immobilized transaminase resin (15.02 g) was combined with a mixture of (1S,5R)-6,8-Dioxabicyclo[3.2.1]octan-4-one (2) (10.04 g, 78 mmol), isopropylamine (5.77 g, 98 mmol)), and water-saturated isopropyl acetate (60 mL). A SpinChem® S2 RBR, with the internal retaining mesh removed, was placed into the reactor, and progressively spun up to approximately 400 rpm to load the resin into the RBR, rotation was maintained throughout the reaction. The vessel was heated to 60° C. and aged for approximately 75 h. At the end of the reaction, the reaction stream was cooled to room temperature and the reaction stream recovered by filtration to yield a solution of Compound 3 (68.97 g, 10.2 wt % 3, 10.5:1 d.r.).

The solution was concentrated under reduced pressure to a final volume of 13 mL. 2-methyl THF (50 mL) was added, and the solution was again concentrated under reduced pressure to a final volume of 13 mL. 2-methyl THF (50 mL) and water (127 uL) were added, and the solution was heated to 40° C. A hydrochloric acid solution (3 M in CPME) was then added over 2 h. After aging an additional 2 h at 40° C. the resulting slurry was cooled to room temperature and aged overnight. The slurry was then filtered and the solid washed with 2-methyl THF. The solid was dried under vacuum/$N_2$ sweep to provide 3b as a solid (6.57 g, 49.3% yield, 38:1 dr). $^1$H NMR (DMSO-$d_6$, 500 MHz) δ 8.26 (br s, 3H), 5.45 (s, 1H), 4.59 (s, 1H), 3.97 (d, J=7.3 Hz, 1H), 3.73-3.58 (m, 1H), 3.06 (s, 1H), 2.12-1.99 (m, 2H), 1.68-1.52 (m, 1H), 1.45-1.42 (m, 1H) ppm: $^{13}$C NMR (DMSO-$d_6$, 125 MHz) δ 98.6, 73.0, 66.9, 47.3, 23.2, 18.6 ppm.

Example 1G: Preparation of (1S,4R,5R)-6,8-Dioxabicyclo[3.2.1]octan-4-hydrobromide (3c)

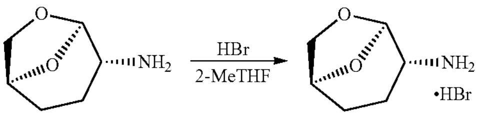

3 3c

A 9.86 wt % solution of (1S,4R,5R)-6,8-dioxabicyclo[3.2.1]octan-4-amine 3a (87.9 g, 67.1 mmol) in 2 MeTHF was charged into a round bottom flask and then concentrated under reduced pressure. 2-MeTHF (50 mL) was added and the process was repeated to remove water and isopropylamine. 2 MeTHF (70 mL) was added followed by a slow addition of aqueous HBr (9.1 mL, 81.0 mmol) at 40° C. The biphasic mixture was then concentrated at 40° C., 2-MeTHF (50 mL) was then added, and the process was repeated to remove excess water. The residue was dissolved in 2-MeTHF (50 mL) and heated to 40° C. Methanol (5 mL) was added and the solution was allowed to cool to room temperature overnight. The resulting slurry was filtered and washed 2-MeTHF (2×20 mL). The isolated solid was recrystallized from 2MeTHF (60 mL) and methanol (6 mL) at 40° C., followed by a recrystallization in methanol (25 mL) at 60° C. 2 MeTHF (10 mL) was added at room temperature to improve the recovery. The resulting solid was filtered, washed with 2-MeTHF (2×20 mL) and dried to yield compound 3c as a white solid (7.86 g, 100 wt %, >200 d.r.). $^1$H NMR (500 MHz, DMSO-d6) δ 8.09 (s, 3H), 5.42 (s, 1H), 4.60 (d, J=4.6 Hz, 1H), 3.98 (dd, J=7.3 Hz, J=0.6 Hz, 1H), 3.74-3.60 (m, 1H), 3.16-3.03 (m, 1H), 2.19-1.83 (m, 2H), 1.67-1.50 (m, 1H), 1.49-1.36 (m, 1H) ppm; $^{13}$C NMR (126 MHz, DMSO-d6) δ 98.52, 73.02, 67.00, 47.36, 23.24, 18.54.

Example 2A: Preparation of (3R,6S)-6-(Hydroxymethyl)oxan-3-aminium 4-methylbenzene-1-sulfonate (4a)

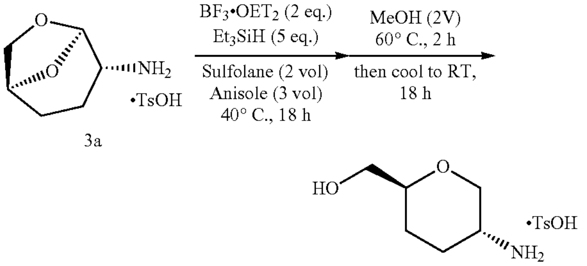

3a

4a (1S,4R,5R)-6,8-Dioxabicyclo[3.2.1]octan-4-aminium 4-methylbenzene-1-sulfonate (3a) (1.5 kg, 4.98 mol, 96:4 dr) was suspended in a mixture of sulfolane (3.00 L) and anisole (4.50 L) at room temperature and the mixture was placed under an atmosphere of nitrogen and agitated with overhead stirring. Triethylsilane (3.98 L, 24.89 mol) was then charged followed by boron trifluoride diethyl etherate (1.26 L, 9.95 mol) and the mixture was heated to 40° C. for ca. 18 hours. The resulting homogenous solution was quenched with MeOH (2.00 L) at such a rate so as to maintain the internal temperature below 45° C. before the subsequent quenched solution was heated to 60° C. for ca. 2 hours. To this mixture was charged (3R,6S)-6-(Hydroxymethyl)oxan-3-aminium 4-methylbenzene-1-sulfonate (4a) (15 g, 1 mol %) and the resulting seed bed was aged for ca. 1 hour at 60° C. before being cooled to 20° C. over 6 hours and then aged a further 18 hours at this temperature. The slurry was filtered, and the wet cake was washed with a solution of 2:1 v/v 2-MeTHF:MeOH (3.00 L) followed by a solution of 9:1 v/v 2-MeTHF:MeOH (2×3.00 L). The cake was dried under vacuum with $N_2$ sweep for ca. 18 hours to provide 4a (1.14 kg, 76% yield, >500:1 dr). $^1$H NMR (MeOH-$d_4$, 500 MHz) δ 7.71 (d, J=8.1 Hz, 2H), 7.25 (d, J=8.0 Hz, 2H), 4.10 (ddd, J=10.8, 4.4, 2.3 Hz, 1H), 3.53-3.47 (m, 2H), 3.39-3.34 (m, 1H), 3.33 (t, J=10.8 Hz, 1H), 3.17 (tt, J=11.0, 4.4 Hz, 1H), 2.37 (s, 3H), 2.17 (dt, J=12.3, 2.8 Hz, 1H), 1.77-1.73 (m, 1H), 1.60 (app. qd, J=12.5, 4.2 Hz, 1H), 1.47-1.38 (m, 1H) ppm. $^{13}$C NMR (MeOH-$d_4$, 125 MHz) δ 143.5, 141.8, 129.9, 126.9, 79.2, 69.2, 65.6, 48.0, 28.6, 27.0, 21.3 ppm.

Example 2B: Preparation of (3R,6S)-6-(Hydroxymethyl)oxan-3-aminium 4-methylbenzene-1-sulfonate (4a)

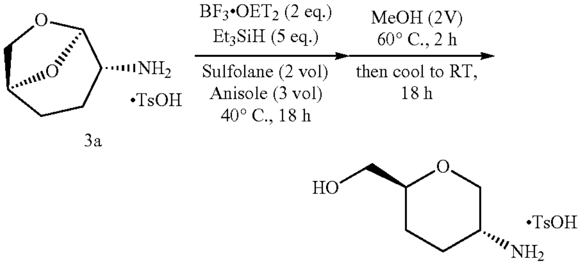

3a

4a (1S,4R,5R)-6,8-Dioxabicyclo[3.2.1]octan-4-aminium 4-methylbenzene-1-sulfonate (3a) (8 g, 26.5 mmol, >99:1 dr) and 2,3-dihydrothiophene 1,1-dioxide (16 mg, 0.2 wt %) were suspended in a mixture of sulfolane (16 mL) and anisole (24 mL) at room temperature and the mixture was placed under an atmosphere of nitrogen and agitated with overhead stirring. Triethylsilane (23.3 L, 146 mmol) was then charged followed by boron trifluoride diethyl etherate (8.1 mL, 63.7 mmol). The vessel was sealed and fitted with a pressure control valve (PCV) set to 50 psig before the mixture was heated to 40° C. for ca. 20 hours. The resulting homogenous solution was quenched with MeOH (16 mL) at such a rate so as to maintain the internal temperature below 45° C. before the subsequent quenched solution was heated to 60° C. for ca. 2 hours. To this mixture was charged (3R,6S)-6-(Hydroxymethyl)oxan-3-aminium 4-methylbenzene-1-sulfonate (4a) (80 mg, 1 wt %) and the resulting seed bed was aged for ca. 1 hour at 60° C. before being cooled to 20° C. over 6 hours and then aged a further 18 hours at this temperature. The slurry was filtered, and the wet cake was washed with a solution of 2:1 v/v 2-MeTHF:MeOH (16 mL) followed by a solution of 9:1 v/v 2-MeTHF:MeOH (2×16 mL). The cake was dried under vacuum with $N_2$ sweep for ca. 18 hours to provide 4a (6.0 g, 74% yield, >500:1 dr).

Example 2C: Preparation of (3R,6S)-6-(Hydroxymethyl)oxan-3-aminium hydrochloride (4b)

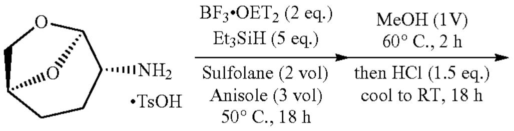

3a

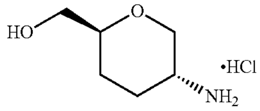

4b (1S,4R,5R)-6,8-Dioxabicyclo[3.2.1]octan-4-aminium 4-methylbenzene-1-sulfonate (3a) (10.0 g, 33.2 mmol, 96:4 dr) was suspended in a mixture of sulfolane (20 mL) and anisole (30 mL) at room temperature and the mixture was placed under an atmosphere of nitrogen and agitated with overhead stirring. Triethylsilane (15.9 mL, 100 mmol) was then charged followed by boron trifluoride diethyl etherate (8.4 mL, 66.4 mmol) and the mixture was heated to 50° C. for ca. 18 hours. The resulting homogenous solution was quenched with MeOH (10 mL) at such a rate so as to maintain the internal temperature below 45° C. before the subsequent quenched solution was heated to 60° C. for ca. 2 hours. HCl (4M in dioxane, 12.5 mL) was slowly charged and the mixture was seeded with (3R,6S)-6-(Hydroxymethyl)oxan-3-aminium hydrochloride (4b) (112 mg, 2 wt %) before being slowly cooled to RT and aged for ca. 18 hours. The slurry was filtered, and the wet cake was washed with 2-MeTHF (2×20 mL). The cake was dried under vacuum with $N_2$ sweep for ca. 18 hours to provide 4b (4.87 g, 88% yield, >100:1 dr). $^1$H NMR (MeOH-$d_4$, 500 MHz) δ 4.13 (ddd, J=10.8, 4.4, 2.3 Hz, 1H), 3.55-3.48 (m, 2H), 3.43-3.38 (m, 1H), 3.37 (t, J=10.8 Hz, 1H), 3.21 (ddd, J=15.3, 11.0, 4.1 Hz, 1H), 2.21 (dt, J=12.2, 2.8 Hz, 1H), 1.79 (app. dq, J=13.4, 3.5, 3.0 Hz, 1H), 1.64 (app. qd, J=12.5, 4.2 Hz, 1H), 1.51-1.42 (m, 1H) ppm. $^{13}$C NMR (MeOH-$d_4$, 125 MHz) δ 79.3, 69.2, 65.6, 48.0, 28.7, 27.1 ppm.

Example 2D: Preparation of (3R,6S)-6-(Hydroxymethyl)oxan-3-aminium hydrochloride (4b)

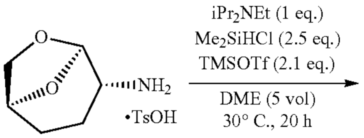

3a

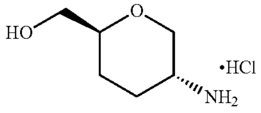

4b (1S,4R,5R)-6,8-dioxabicyclo[3.2.1]octan-4-amine 4-methylbenzenesulfonate 3a (10 g, 33.2 mmol, >100:1 dr) was suspended in DME (50 mL) at room temperature and the mixture was placed under an atmosphere of nitrogen and agitated with magnetic stirring. N,N-diisopropylethylamine (5.80 mL, 33.2 mmol, 1.0 eq.) was then charged in one portion and the batch was agitated at room temperature for ca. 5 minutes. Chlorodimethylsilane (14.74 mL, 133 mmol, 4.0 eq.) was slowly charged followed by trimethylsilyl trifluoromethanesulfonate (12.59 mL, 69.7 mmol, 2.1 eq) and the mixture was heated to 30° C. for ca. 20 hours. The resulting homogenous solution was quenched with water (4.18 mL, 232 mmol, 7 eq.) and the phases were separated. The bottom layer was cooled to RT before being seeded with ((2S,5R)-5-aminotetrahydro-2H-pyran-2-yl)methanol hydrochloride (100 mg, 1 wt %). 2-Methyltetrahydrofuran (30 mL) was then charged to the resulting slurry over ca. 30 minutes and the mixture was aged for ca. 18 hours at RT. The slurry was filtered and the wet cake was washed with 2-MeTHF (2×20 mL). The cake was dried under vacuum with N2 sweep for ca. 18 hours to provide 4b (3.13 g, 56% yield, >100:1 dr). 1H NMR (MeOH-d4, 500 MHz) δ 4.13 (ddd, J=10.8, 4.4, 2.3 Hz, 1H), 3.55-3.48 (m, 2H), 3.43-3.38 (m, 1H), 3.37 (t, J=10.8 Hz, 1H), 3.21 (ddd, J=15.3, 11.0, 4.1 Hz, 1H), 2.21 (dt, J=12.2, 2.8 Hz, 1H), 1.79 (app. dq, J=13.4, 3.5, 3.0 Hz, 1H), 1.64 (app. qd, J=12.5, 4.2 Hz, 1H), 1.51-1.42 (m, 1H). 13C NMR (MeOH-d4, 125 MHz) δ 79.3, 69.2, 65.6, 48.0, 28.7, 27.1.

3. Synthesis of Compound 7

A. Synthesis Without Lithium Bromide Additive

Example 3A: (2-Chloro-4-phenoxyphenyl)(4-chloro-7H-pyrrolo[2,3-d]pyrimidin-5-yl)methanone (7)

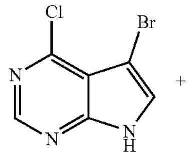

5

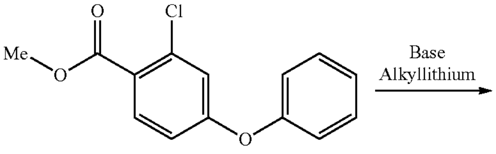

6

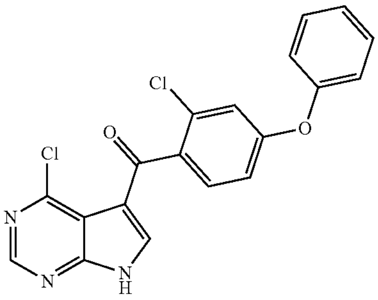

7

To a slurry of 5-Bromo-4-chloro-7H-pyrrolo[2,3-d]pyrimidine (5) (5.0 g, 21.5 mmol) in THF (60 mL) at −35° C. was added methyllithium in diethyl ether (1.6 M, 14.1 mL, 22.6 mmol) maintaining the temperature below −30° C. The mixture was then cooled to below −65° C. and n-Butyllithium in hexanes (2.7 M, 8.4 mL, 22.6 mmol) was added dropwise maintaining the reaction temperature below −60° C. and the resulting slurry was stirred for 1 h. Then, a solution of Methyl 2-chloro-4-phenoxybenzoate (6) (5.71 g, 21.72 mmol) in THF (10 mL) was added dropwise maintaining the temperature below −60° C. The resulting mixture was stirred at this temperature for an additional 1.5 h, quenched by addition of acetic acid (2.7 mL, 47.3 mmol) and then warmed to room temperature. The mixture was washed with water (37.5 mL) and the layers were separated. THF was removed under vacuum and replaced with Ethanol (70 mL). The resulting slurry was aged at room temperature, filtered and the solids were washed with Ethanol (25 mL) to yield 7 (6.71 g, 81% yield) after drying. $^{1}H$ NMR (500 MHz, DMSO-$d_6$) δ 13.40 (s, 1H), 8.74 (s, 1H), 8.12 (s, 1H), 7.59 (d, J=8.5 Hz, 1H), 7.48 (tt, J=7.5 Hz, J=2.2 Hz, 2H), 7.29-7.23 (tt, J=7.5 Hz, J=1.1 Hz, 1H), 7.22-7.14 (m, 3H), 7.01 (dd, J=8.5 Hz, J=2.4 Hz, 1H) ppm. $^{13}C$ NMR (126 MHz, DMSO-$d_6$) δ 185.9, 159.1, 155.1, 154.0, 1511.9, 151.8, 138.4, 134.0, 132.1, 131.8, 130.4, 124.8, 119.7, 119.2, 116.2, 115.4, 113.9 ppm.

B. Synthesis of Compound 7 with Lithium Bromide in a Flow Reactor

Example 3B: (2-Chloro-4-phenoxyphenyl)(4-chloro-7H-pyrrolo[2,3-d]pyrimidin-5-yl)methanone (7)

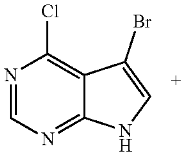

5

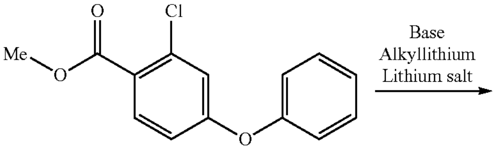

6

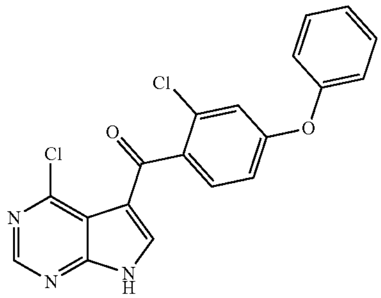

7

Preparation of Solution A: 5-Bromo-4-chloro-7H-pyrrolo[2,3-d]pyrimidine (5) (1.20 kg, 5.16 mol) and lithium bromide (1.57 kg, 18.12 mol) were dissolved in THF (27 L). The mixture was stirred until a homogenous solution was generated. The resulting water content of the solution was 250 ppm (7.2 mol %). The mixture was cooled to −27° C. and methyllithium in diethoxymethane (2.88 M, 1.92 L, 5.53 mol) was added dropwise. The mixture was warmed to room temperature to yield a 0.173 M solution of 5.

Preparation of Solution B: Solution B containing commercially available n-Butyllithium in hexanes (1.435 M).

Preparation of Solution C: Methyl 2-chloro-4-phenoxy benzoate (6) (1.356 kg, 5.162 mol) was dissolved in THF (9.183 kg).

Preparation of Solution D: To a 10 wt % aqueous NaCl (9.0 L) solution was added acetic acid (1.11 L).

Solution A containing Compound 5 (0.173 M, 3.90 kg/h) and Solution B containing n-butyllithium in hexanes (1.435 M, 5.91 g/min) were pre-cooled and combined at −27° C. for a total of 0.727 min in a 56.09 mL stainless steel plug flow reactor (PFR). The resulting AB stream was then combined with Solution C containing Compound 6 (0.468 M, 1.53 kg/h) for a total of 2.074 min in a 215 mL PFR, before being quenched with Solution D. The resulting biphasic mixture was collected, the phases were separated.

The organic layer containing 1.38 kg of 7 was heated to 30° C. and concentrated to 11 L under vacuum. The resulting slurry was heated to 45-50° C. and aged for 30 minutes. An ethanol:water (2/3, v/v) mixture (17.8 L) was added over 3 hours while maintaining an internal temperature of 45-50° C. The slurry was allowed to cool to room temperature and stirred overnight. The mixture was filtered, and the solids were washed three times with ethanol (4.1 L) and dried under vacuum with a stream of nitrogen to provide Compound 7 (1.25 kg, 75% yield based on the amount of Compound 5 flowed, 63% yield based on the amount of 5 charged). 1H NMR (500 MHz, DMSO-$d_6$) δ 13.40 (s, 1H), 8.74 (s, 1H), 8.12 (s, 1H), 7.59 (d, J=8.5 Hz, 1H), 7.48 (tt, J=7.5 Hz, J=2.2 Hz, 2H), 7.29-7.23 (tt, J=7.5 Hz, J=1.1 Hz, 1H), 7.22-7.14 (m, 3H), 7.01 (dd, J=8.5 Hz, J=2.4 Hz, 1H) ppm. $^{13}$C NMR (126 MHz, DMSO-$d_6$) δ 185.9, 159.1, 155.1, 154.0, 1511.9, 151.8, 138.4, 134.0, 132.1, 131.8, 130.4, 124.8, 119.7, 119.2, 116.2, 115.4, 113.9 ppm.

Example 4A: (2-Chloro-4-phenoxyphenyl)(4-{[(3R, 6S)-6-(hydroxymethyl)oxan-3-yl]amino}-7H-pyrrolo[2,3-d]pyrimidin-5-yl)methanone (A)

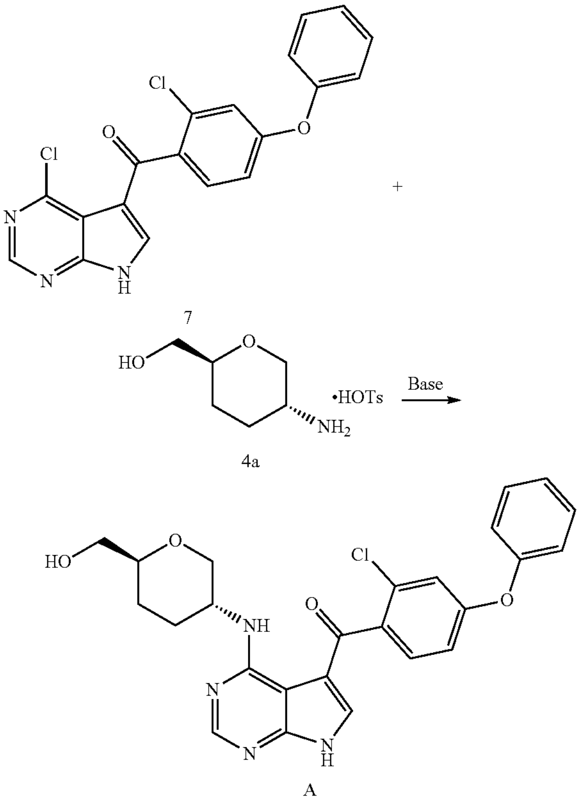

7

4a

A (2-Chloro-4-phenoxyphenyl)(4-chloro-7H-pyrrolo[2,3-d] pyrimidin-5-yl)methanone (7) (0.5 kg, 1.3 mol) and (3R, 6S)-6-(Hydroxymethyl)oxan-3-aminium 4-methylbenzene-1-sulfonate (4a) (434 g, 1.43 mol) were slurried in ethanol (4 L, 8 V). N,N-Diisopropylethylamine (DIPEA) (420 g, 3.25 mol) was added and the reaction mixture was heated to 80° C. and agitated for 12 hours. The reaction was cooled to 55-65° C. and water (2 L, 2 V) was added. The solution was passed through a polishing filter followed by a flush with ethanol/water=4/1 (v/v, 0.5 L, IV). The filtered solution was then cooled to 35±5° C., product seed was added (1 g, 0.2 wt %) and the mixture was aged for at least 15 min. Additional water (5.5 L, 11 V) was added over 10 hours and the mixture was aged for 3-5 hours at 35±5° C. and then cooled to 20° C. over at least 1 hour. Acetic acid (37 mL, 0.5 equiv) was added dropwise at 25° C. until a pH of 6-8 was reached. The slurry was then aged for at least 3-5 hours at 20° C. until the desired supernatant concentration was obtained. The slurry was filtered, and the product was washed three times with 2:3 (v/v) ethanol:water (1 L). The wet cake was dried under vacuum and nitrogen flow at ≤50° C. yielding Compound A (557 g, 89% yield). $^{1}$H NMR (600 MHz, DMSO-$d_6$) δ 12.78 (s, 1H), 8.63 (d, J=7.1 Hz, 1H), 8.28 (s, 1H), 7.65 (s, 1H), 7.59 (d, J=8.4 Hz, 1H), 7.52-7.45 (m, 2H), 7.26 (tt, J=7.3, 1.1 Hz, 1H), 7.22-7.17 (m, 3H), 7.03 (dd, J=8.4, 2.4 Hz, 1H), 4.69 (s, 1H), 4.22-4.13 (m, 2H), 3.48-3.42 (m, 1H), 3.41-3.34 (m, 2H), 3.18-3.11 (m, 1H), 2.25-2.17 (m, 1H), 1.79 (dq, J=15.1, 3.2 Hz, 1H), 1.60 (qd, J=12.3, 3.9 Hz, 1H), 1.41 (tdd, J=13.3, 10.5, 3.9 Hz, 1H) ppm. $^{13}$C NMR (151 MHz, D DMSO-$d_6$) δ 189.65, 158.59, 156.25, 155.19, 154.10, 152.71, 136.08, 133.32, 131.17, 130.78, 130.27, 124.62, 119.59, 119.04, 116.35, 116.11, 100.54, 77.69, 69.82, 64.24, 46.18, 29.29, 27.06 ppm.

Example 4B: (2-Chloro-4-phenoxyphenyl)(4-{[(3R, 6S)-6-(hydroxymethyl)oxan-3-yl]amino}-7H-pyrrolo[2,3-d]pyrimidin-5-yl)methanone (A)

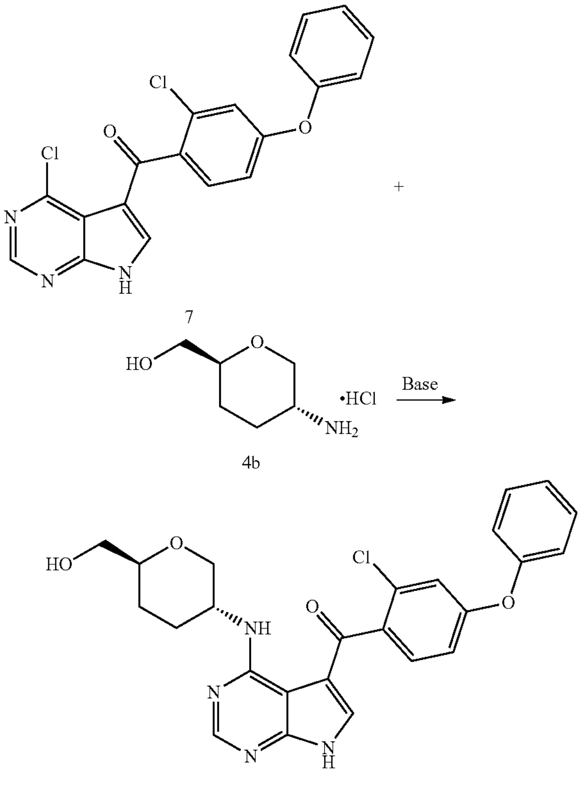

7

4b

A

Under nitrogen atmosphere, (2-Chloro-4-phenoxyphenyl) (4-chloro-7H-pyrrolo[2,3-d]pyrimidin-5-yl)methanone (7) (1.0 g, 2.6 mmol) and (3R,6S)-6-(Hydroxymethyl)oxan-3-aminium chloride (4b) (0.48 g, 2.86 mmol) were slurried in ethanol (10 mL, 10 V). N,N-Diisopropylethylamine (DIPEA) (0.84 g, 6.51 mmol) was added and the reaction mixture was heated to 80° C. and agitated for 18 hours. The reaction was cooled to 45-55° C. and water (2.5 mL, 2.5 V) was added. The reaction was further cooled to 35±5° C. A solution of acetic acid (0.094 g, 0.6 equiv) in water (7.5 mL, 7.5 V) was added over 5 hours, and the mixture was aged for 1-2 hours at 35±5° C., before cooled to 20° C. over at least 1 hour. The slurry was then aged overnight for 10-15 hours at 20° C. until the desired supernatant concentration was obtained. The slurry was filtered, and the product was washed two times with 1/1 (v/v) ethanol:water (5 mL). The wet cake was dried under vacuum and nitrogen flow at ≤50° C. yielding Compound A (1.055 g, 85% yield). $^1$H NMR (600 MHz, DMSO-$d_6$) δ 12.78 (s, 1H), 8.63 (d, J=7.1 Hz, 1H), 8.28 (s, 1H), 7.65 (s, 1H), 7.59 (d, J=8.4 Hz, 1H), 7.52-7.45 (m, 2H), 7.26 (tt, J=7.3, 1.1 Hz, 1H), 7.22-7.17 (m, 3H), 7.03 (dd, J=8.4, 2.4 Hz, 1H), 4.69 (s, 1H), 4.22-4.13 (m, 2H), 3.48-3.42 (m, 1H), 3.41-3.34 (m, 2H), 3.18-3.11 (m, 1H), 2.25-2.17 (m, 1H), 1.79 (dq, J=15.1, 3.2 Hz, 1H), 1.60 (qd, J=12.3, 3.9 Hz, 1H), 1.41 (tdd, J=13.3, 10.5, 3.9 Hz, 1H) ppm. $^{13}$C NMR (151 MHz, D DMSO-$d_6$) δ 189.65, 158.59, 156.25, 155.19, 154.10, 152.71, 136.08, 133.32, 131.17, 130.78, 130.27, 124.62, 119.59, 119.04, 116.35, 116.11, 100.54, 77.69, 69.82, 64.24, 46.18, 29.29, 27.06 ppm.

Example 5: Enzyme Preparation as Lyophilized Cell-Free Lysate Powder 25 mL of LB broth supplemented with 34 micrograms per mL chloroamphenicol and 1% (w/v) glucose was inoculated with 20 microliters of a glycerol stock of *E. coli* W3110 strain cells harboring plasmid encoding for transaminase in the pCK110900 vector. Cells were grown until saturation for 18 hours at 30° C./250 RPM. The following day, a 2.8 L flask containing 1 L of TB supplemented with 34 micrograms per mL of chloroamphenicol and 0.1 mM pyridoxine was subcultured with the overnight saturated culture to an initial OD600 of 0.05. This culture was grown at 30° C./250 RPM for ~2.5 hours until the OD600 reached 0.6-0.8. Protein production was induced with 1 mM IPTG for 20 hours at 30° C./250 RPM. Cells were pelleted by centrifugation and the supernatants were discarded. Cell pellets were flash frozen in liquid nitrogen, thawed and resuspended with 5 mL (per gram of pellet) of ice-cold 50 mM triethanolamine-HCl buffer pH 7.5 supplemented with 0.1 mM PLP. This suspension was shaken at 20° C. for 30 minutes, after which time the cells were placed on ice to chill, and then disrupted by high-pressure homogenization (16,000 PSI). The resulting lysate was then clarified by centrifuging at 10,000×g for 45 minutes at 4° C. Following centrifugation, the supernatant was frozen and lyophilized. This protocol may be followed to prepare any transaminase enzyme of SEQ ID NO: 1 through SEQ ID NO: 8.

It will be appreciated that various of the above-discussed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A process for preparing Compound 3

3

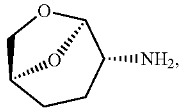

or a pharmaceutically acceptable salt thereof, comprises the steps of:

a) combining a co-factor in a buffer solution or water with isopropylamine and a transaminase enzyme to produce a reagent mixture; and b) adding Compound 2

2

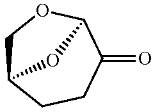

to the reagent mixture to produce a solution comprising Compound 3.

2. The process of claim 1, further comprising the steps of a) adding an inorganic base to adjust the pH of a solution comprising Compound 3 to about 12 to about 14;

b) adding a solvent and an inorganic salt to produce a biphasic resulting mixture comprising Compound 3, said biphasic mixture comprising an organic layer and an aqueous layer;

c) separating the organic layer from the biphasic resulting mixture with a solvent;

d) combining the organic layers of the biphasic resulting mixture with a solution of an acid in a solvent, to produce a slurry comprising Compound 3'

3'

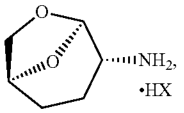

wherein HX is selected from a pharmaceutically acceptable acid; and e) filtering the slurry to obtain compound 3' as a solid.

3. The process of claim 2, wherein HX is p-toluenesulfonic acid, further comprising, in step d, combining a solution of p-toluenesulfonic acid in a solvent with the organic layers of the resulting biphasic mixture to produce a slurry comprising Compound 3a; and filtering the slurry to obtain Compound 3a as a solid.

4. A process for preparing Compound 3'

3'

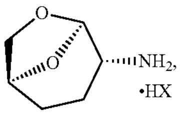

wherein HX is a pharmaceutically acceptable acid, comprising the steps of:

a) combining a transaminase enzyme with a buffer solution or water, and a solid support, followed by incubation to prepare an immobilized transaminase enzyme;

b) washing the immobilized transaminase enzyme with a buffer solution or water;

c) washing with a transamination solvent;

d) combining Compound 2 with isopropylamine and transamination solvent to provide a reaction stream;

e) combining the reaction stream with the immobilized transaminase enzyme to produce a slurry comprising Compound 3;

f) separating the slurry comprising Compound 3 from the immobilized transaminase enzyme to produce a solution comprising Compound 3;

g) combining the solution comprising Compound 3 with a solution of an acid in a transamination solvent to produce a slurry comprising Compound 3'; and h) filtering the slurry to obtain Compound 3' as a solid.

5. The process of claim 4, further comprising the step of washing the immobilized transaminase enzyme with water and then washing the immobilized transaminase enzyme with an isopropanol:PEG-400:water mixture.

6. The process of claim 4, further comprising the step of combining Compound 2 with isopropylamine in a water-containing transamination solvent to prepare the reaction stream in step d).

7. The process of claim 4, further comprising performing steps b), c) and e) in a continuous reaction system wherein the buffer solution or water, the transamination solvent and the reaction stream are continuously passed over the immobilized transaminase enzyme.

8. The process of claim 7, wherein the continuous reaction system is a packed-bed reactor (PBR).

9. The process of claim 4, further comprising the steps of:

a) distilling the solution comprising compound 3 to remove isopropylamine and water to produce a resulting solution comprising compound 3; and b) adding water to the resulting solution comprising compound 3 to adjust the water content to about 0 to about the water saturation point of the transamination solvent.

10. The process of claim 4 wherein HX is p-toluenesulfonic acid, further comprising the steps of combining the solution comprising Compound 3 with a solution of p-toluenesulfonic acid in a transamination solvent to produce a slurry comprising Compound 3a 3a

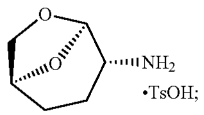

and filtering the slurry to isolated 3a as a solid.

11. A process for preparing Compound 4'

4'

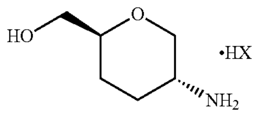

wherein HX is a pharmaceutically acceptable acid, comprising the steps of:

a) adding Compound 3' to a weakly coordinating solvent;

b) adding a silane reductant or a borane reductant, and a Lewis acid and heating to about 30 to about 70° C. to produce a resulting solution;

c) adding an alcohol to produce a solution comprising Compound 4';

d) cooling the solution to produce a slurry comprising Compound 4'; and e) filtering the slurry to obtain Compound 4' as a solid.

12. The process of claim 11, further comprising the step of adding a pharmaceutically acceptable acid, after adding the alcohol in step c), to obtain a pharmaceutically acceptable salt of Compound 4'.

13. The process of claim 11, wherein HX is p-toluenesulfonic acid, further comprising the step of adding Compound 3a to a weakly coordinating solvent in step a) and producing a solution comprising Compound 4a 4a

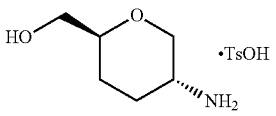

in step c).

14. The process of claim 13, wherein the weakly coordinating solvent in step a) is a mixture of anisole and sulfolane, the silane reductant in step b) is triethyl silane and the Lewis acid in step b) is boron trifluoride diethyl etherate, and the ratio of triethyl silane to boron trifluoride diethyl etherate is less than 3:1.

15. The process of claim 14, wherein 2,3-dihydrothiophene 1,1-dioxide or 2,5-dihydrothiophene 1,1-dioxide is also added in step a).

16. The process of claim 14, wherein in step b), adding triethyl silane and boron trifluoride diethyl etherate and heating in a reactor to about 30 to about 70° C. to produce a resulting solution, wherein said reactor is a sealed reactor or in a reactor capable of controlling the reaction pressure.

17. A process for preparing Compound 4b comprising the steps of:

a) adding Compound 3' to an organic solvent;

b) adding an organic base to produce a reaction mixture;

c) adding a silane reductant and trimethylsilyl trifluoromethanesulfonate to the reaction mixture to produce a resulting solution;

d) adding water to the resulting solution to create a two-layer mixture comprising Compound 4b, said two-layer mixture having a top layer and a bottom layer, and separating the bottom from the two-layer mixture comprising Compound 4b;

e) cooling the bottom phase to produce a resulting slurry; and f) filtering the slurry to obtain Compound 4b as a solid.

* * * * *